United States Patent [19]

Shaber et al.

[11] Patent Number: 5,397,768
[45] Date of Patent: Mar. 14, 1995

[54] FUNGICIDAL AND HERBICIDAL TRIAZOLES

[75] Inventors: Steven H. Shaber, Horsham, Pa.; Luong T. Nguyen, Pinewood Garden, Singapore

[73] Assignee: Rohm and Haas Company, Philadelphia, Pa.

[21] Appl. No.: 130,476

[22] Filed: Oct. 1, 1993

Related U.S. Application Data

[62] Division of Ser. No. 904,751, Jun. 25, 1992, Pat. No. 5,264,415.

[51] Int. Cl.$^6$ .................. A01N 43/653; A01N 43/40; C07D 409/14; C07D 407/14
[52] U.S. Cl. ..................... 504/272; 504/253; 504/273; 504/274; 514/340; 514/383; 514/384; 514/184; 546/276; 548/263.2; 548/263.4; 548/263.6; 548/263.8; 548/264.2; 548/264.4; 548/264.8; 548/265.2; 548/266.4; 548/101
[58] Field of Search ............... 514/340, 383, 384, 184; 504/253, 272, 273, 274; 546/276; 548/101, 263.2, 263.4, 263.6, 263.8, 264.2, 264.4, 264.8, 265.2, 266.4

[56] References Cited

U.S. PATENT DOCUMENTS

| | | | |
|---|---|---|---|
| 4,366,165 | 12/1982 | Miller et al. | 424/269 |
| 4,398,942 | 8/1983 | Ikari et al. | 71/92 |
| 4,411,687 | 10/1983 | Zeeh et al. | 71/76 |
| 4,598,085 | 7/1986 | Heeres et al. | 514/383 |
| 4,663,463 | 5/1987 | Kunz et al. | 548/267.6 |
| 4,789,747 | 12/1988 | Husslein et al. | 548/267.6 |

FOREIGN PATENT DOCUMENTS

| | | |
|---|---|---|
| 69448 | 1/1983 | European Pat. Off. . |
| 2104065 | 3/1983 | United Kingdom . |

OTHER PUBLICATIONS

Imperial Chemical, CA: 98244x, 1983.

*Primary Examiner*—Patricia L. Morris
*Attorney, Agent, or Firm*—Clark R. Carpenter

[57] ABSTRACT

Compounds of the formula

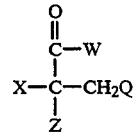

are fungicides and herbicides when Z is alkyl, cycloalkyl, aryl, or aralkyl; Q is a triazolyl; X is an aryl group or a heterocyclic group; and W is a variety of functional groups.

9 Claims, No Drawings

FUNGICIDAL AND HERBICIDAL TRIAZOLES

This is a division of application Ser. No. 07/904,751, filed Jun. 25, 1992, and issued on Nov. 23, 1993, as U.S. Pat. No. 5,264,415.

FIELD OF THE INVENTION

This invention relates to (2-carboxy-2,2-disubstituted)-ethyl-1,2,4-triazoles, their enantiomorphs, acid addition salts and metal salt complexes, compositions containing these compounds and the use of these compounds as herbicides and as fungicides, particularly against phytopathogenic fungi.

DESCRIPTION OF RELATED ART

U.S. Pat. No. 4,366,165 discloses 1- and 4-arylcyanoalkyl-1,2,4- triazoles as fungicidal agents. The compounds of this disclosure are limited to those having a cyano group bonded to the beta carbon of the alkyl substituent on the triazole.

European Patent Publication No. 52,424 discloses 2-ethyl substituted triazole compounds in which the beta carbon of the ethyl group has a chloro, cyano, or oxy substituent.

U.K. Patent Application No. GB 2104065A discloses microbial mandelic acid derivatives and mandelonitriles. These compounds are generally 2-ethyltriazoles in which the beta carbon of the ethyl group is substituted by an aromatic substituent, an oxy substituent, and a carboxyl or cyano group. All of the compounds of this disclosure require that at least one of the substituents on the beta carbon of the ethyl group be an oxy substituent.

U.S. Pat. No. 4,598,085 discloses fungicidal 1-(2-aryl-2-R-ethyl)-1H-1,2,4-triazoles as fungicidal agents. The compounds of this disclosure all have a hydrogen atom on the beta carbon of the ethyl substituted triazole in addition to an optionally substituted phenyl group and lower alkyl, cycloalkyl, lower alkenyl, aryl methyl and aryl ethyl substituents.

German Patent Publication 3408127 discloses fungicidal N-(azolylethyl)carboxamides. The compounds of this disclosure reportedly have a carboxamide group attached to the beta carbon of the ethyl substituent of the triazole.

U.S. Pat. No. 4,398,942 discloses herbicidally active phenylacetonitriles. These compounds, while being substituted ethyltriazoles, have either a cyano or ethynyl group on the beta carbon of the ethyl substituent.

U.S. Pat. No. 4,411,687 discloses fungicidal azolyl glycol derivatives having ether or ester linkages at the beta carbon of 2-ethyltriazoles, along with a glycol substituent on the alpha carbon.

German Patent Publication 3221915 discloses fungicidal esters having chloro substitutents on the alpha carbon of 2-ethyltriazoles and alkyl esters on the beta carbon.

European Patent Publication 69,448 discloses fungicidal triazoles having amido substituents on the beta carbon of 2-ethyltriazoles.

European Patent Publication 234,242 discloses fungicidal 2-ethyltriazoles with fluoroalkyloxy substituents on the beta carbon of the ethyl chain.

European Patent Publication No. 46,658 discloses bistriazolyl ketones in which the bridging ethylene has a lower alkyl carbonyl substituent.

SUMMARY OF THE INVENTION

This invention relates to novel (2-carboxy-2,2-disubstituted)ethyl-1,2,4-triazoles, the enantiomorphs, acid addition salts and metal salt complexes thereof, and their use as broad-spectrum systemic fungicides. Certain compounds of this invention are also useful as pre- and postemergent herbicides.

In particular, this invention relates to compounds of the formula

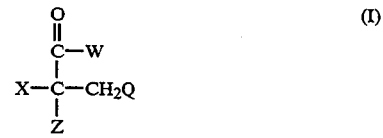

wherein
X is optionally substituted aryl or optionally substituted heterocyclyl such as pyridyl, pyrimidinyl, pyrazinyl, thienyl and furyl;
Q is optionally substituted 1-(1,2,4-triazolyl) or 4-(1,2,4-triazolyl);
Z is cyano, alkoxycarbonyl, alkyl, haloalkyl, alkenyl, haloalkenyl, alkynyl, cycloalkyl, cycloalkenyl, cycloalkylalkyl, aryl, aralkyl, heterocyclyl or heterocyclylalkyl, provided X and Z are not heterocyclyl at the same time;
W is —OK, an optionally substituted alkoxy or amino, or an oxygen completing a lactone with the X group; and
the agronomically acceptable enantiomorphs, acid addition salts and metal salt complexes thereof.

DETAILED DESCRIPTION OF THE INVENTION

In particular, this invention relates to compounds of the formula:

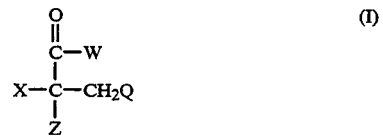

wherein
X is optionally substuted aryl for example, phenyl and naphthyl, or optionally substituted heterocyclyl for example pyridyl, pyrimidinyl, pyrazinyl, thienyl and furyl;
Q is optionally substituted 1-(1,2,4-triazolyl) or 4-(1,2,4-triazolyl);
Z is cyano, alkoxycarbonyl, ($C_1$–$C_{12}$)alkyl, halo($C_1$–$C_{12}$)alkyl, ($C_2$–$C_8$)alkenyl, halo($C_2$$C_8$)alkenyl, ($C_2$–$C_8$)alkynyl, ($C_3$–$C_8$)cycloalkyl,($C_5$–$C_8$)cycloalkenyl, cycloalkylalkyl, aryl, aralkyl, heterocyclyl or heterocyclylalkyl, provided X and Z are not heterocyclyl at the same time.
W is —OK, —OR, —OR'OR", —OR'Y, —OR'-COOR", —OR'OCOR", —NB$_2$, morpholinyl, piperidinyl, alkyl substituted piperidinyl, or an oxygen completing a lactone when joined with X;
B is independently selected from hydrogen, ($C_1$–$C_{12}$)alkyl, hydroxy($C_3$–$C_5$)alkyl or ($C_2$–$C_6$)alkenyl;
R is ($C_1$–$C_{12}$)alkyl, X, ($C_3$–$C_8$)alkenyl, ($C_3$–$C_8$)alkynyl, ($C_3$–$C_8$)cycloalkyl($C_1$–$C_5$)alkyl, cyanoalkyl, hydroxy($C_2$–$C_4$)alkyl or epoxyalkyl, all which may be optionally halogenated, or is hydrogen, provided that when Z is phenyl, W is not NB$_2$ and when Z is methyl, W is not methoxy;

R' is (—CH(CH$_3$)—)$_p$(—CH$_2$—)$_n$ or (—CH$_2$—)$_q$CH=CH(—CH$_2$—)m;

n is an integer from 0 to 6;

p is 0 or 1, provided n and p are not both 0;

q and m are each independently integers from 0 to 3;

R" is (C$_1$-C$_6$)alkyl, X, Y-alkyl or (C$_1$-C$_2$)trialkylsilyl(C$_1$-C$_4$)alkyl, all which may be optionally halogenated, or hydrogen;

Y is phenyl, naphthyl, piperidinyl, triazolyl, pyrazinyl, phthalimido, morpholinyl, pyridyl, thienyl, furyl or cycloalkyl, all which may be optionally substituted; and the agronomically acceptable enantiomorphs, acid addition salts and metal salt complexes thereof.

The term "aryl" means an aromatic ring structure of from 6 to 10 carbon atoms, preferably a phenyl or a naphthyl group. The aryl may be substituted with up to three substituents, preferably with, represented by T up to two substituents, such as hydroxy, halo, nitro, trihalomethyl, cyano, (C$_1$-C$_4$)alkyl, (C$_1$-C$_4$)alkoxy, (C$_1$-C$_4$)alkylthio, (C$_1$-C$_4$)alkylsulfinyl, (C$_1$-C$_4$)alkylsulfonyl, (C$_1$-C$_4$)alkoxy(C$_1$-C$_4$)alkoxy, (C$_1$-C$_4$)alkylcarbonyl, (C$_2$-C$_8$)alkenyl, (C$_2$-C$_4$)alkenyloxy, (C$_2$-C$_8$)alkynyl, (C$_2$-C$_8$)alkynyloxy, phenyl, phenyl monosubstituted with halo, alkyl or alkoxy, phenoxy and phenoxy monosubstituted with halo, alkyl or alkoxy. Typical aryl groups include, phenyl, naphthyl, 4-chlorophenyl, 4-fluorophenyl, 2-methoxyphenyl, 4-phenylphenyl, 4-(4'-chlorophenyl)phenyl, 4-phenoxyphenyl, 2-chloro-4-(4'-chlorophenoxy)phenyl, 2,4-dibromophenyl, 3,5-difluorophenyl, 2,4,6-trichlorophenyl, 2,3,4-tribromophenyl, 3,4-dichlorophenyl, 2-chloro-4-iodophenyl, 3-chloro-4-nitrophenyl, 2,4-dinitrophenyl, 3,4,5-trimethylphenyl, 2-nitro-4-methoxyphenyl, 2-chloronaphthyl, 2-nitronaphthyl, 2,4-dimethoxyphenyl, 4-(trifluoromethyl)phenyl, 2-nitro-4-(trifluoromethyl)phenyl, 3,5-bis(methylthio)phenyl, 2-cyano-5-methylphenyl, 2,4-bis(methylsulfinyl)phenyl, 2,4-bis-(methylsulfonyl)phenyl, 2,4-diiodonaphtyl and 2-iodo-4-methylphenyl.

The term "heterocyclyl" means 5 and 6 membered rings having up to three different hetero atoms selected from nitrogen, oxygen and sulfur, such as furan, thiophene, triazole, imidazole, pyridine, pyrimidine, pyrazole, oxazole, piperazine and morpholine, which may be optionally substituted with up to two substituents independently selected from alkyl and halo.

The term "alkyl" includes both branched and straight chained alkyl groups of from 1 to 12 carbon atoms. Typical alkyl groups are methyl, ethyl, n-propyl, isopropyl, n-butyl, sec-butyl, isobutyl, t-butyl, n-pentyl, neopentyl, isopentyl, hexyl, heptyl, isooctyl, nonyl, decyl, isodecyl, undecyl, dodecyl and the like. The alkyl groups may be halogenated.

The term "alkylenyl" refers to a bivalent alkyl group in which two free bonds can be on the same carbon or different carbons.

The term "aralkyl" defines a group wherein the alkyl chain is from 1 to 4 carbon atoms, branched or straight chained, and the aryl is defined as above. Typical aralkyl groups include, 2,4-dichlorobenzyl, 2,4-dibromobenzyl, 2,5-dinitrobenzyl, 2,4,6-trichlorobenzyl, 3,5-dimethoxyphenethyl, 2,5-bis(methylsulfonyl)phenethyl, 2,4,5-trimethylphenylbutyl, 2,4-dicyanonaphthylmethyl, 2-nitronaphthylethyl, 2-nitronaphthylpropyl, 2,4-dibromonaphthylbutyl, 4-chlorophenethyl, 4-fluorophenethyl, 4-(trifluoromethyl)phenethyl and the like.

The terms "alkenyl" and "alkynyl" include branched and straight chain hydrocarbons of from 2 to 8 carbon atoms having at least one unsaturated bond. These substituents may be halogenated.

The term "alkenylenyl" refers to a bivalent alkenyl group in which the two free bonds are on different carbons.

In the definition of Q, the term "optionally substituted 1-(1,2,4-triazolyl) or 4-(1,2,4-triazolyl)" includes unsubstituted 1- and 4-(1,2,4-triazolyl) and 1- and 4-(1,2,4-triazolyl) substituted with up to two substituents selected from halo, (C$_1$-C$_4$)alkyl, nitro, cyano, mercapto and (C$_1$-C$_5$)alkylmercapto.

As used herein and in the appended claims, the symbol "OCOR" refers to a group in which the carbon of the carbonyl moiety is bonded to R; the symbol "COOR" refers to a group in which the non-carbonyl oxygen is bonded to the R group.

The acids which can be utilized in making the acid addition salts of the present invention include hydrochloric, hydrobromic, nitric, sulfuric, phosphoric, hydriodic, hydrofluoric, perchloric, p-toluenesulfonic, methanesulfonic, acetic, citric, tartaric, malic, maleic, oxalic, fumaric, phthalic and the like.

Another embodiment of this invention is the metal salt complexes of the formula:

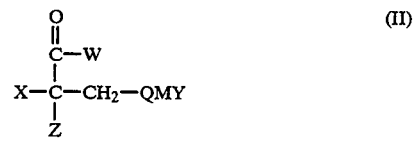

wherein X, Z, Q and W are as defined in Formula (I) above, M is a cation selected from Group IIA, IVA, IB, IIB, IIIB, VIB, VIIB and VIII of the Periodic Table and Y is an anionic counterion selected to neutralize the charge of the cation M.

Typical cations encompassed by this invention are magnesium, manganese, copper, nickel, zinc, iron, boron, cobalt, calcium, tin, cadmium, mercury, chromium, barium and the like.

Typical anions encompassed by this invention are chloride, bromide, iodide, fluoride, sulfate, bisulfate, perchlorate, nitrate, nitrite, phosphate, carbonate, bicarbonate, acetate, citrate, oxalate, tartrate, malate, maleate, fumarate, p-toluenesulfonate, methanesulfonate, mono- or di(C$_1$-C$_4$)alkyldithiocarbamate, (C$_1$-C$_4$)alkylenebisdithiocarbamate and the like.

A preferred embodiment of this invention is the compounds, enantiomorphs, salts and complexes of Formulas (I) and (II) wherein X is phenyl, optionally substituted with from 1 to 3 substituents, preferably with from 1 to 2 substituents, selected from halo, nitro, trihalomethyl, preferably trifluoromethyl, cyano, (C$_1$-C$_4$)alkyl, (C$_1$-C$_4$)alkoxy, (C$_1$-C$_4$)alkylthio, phenoxy, monohalophenoxy and phenyl; Z is selected from (C$_1$-C$_8$)alkyl, halo(C$_1$-C$_{12}$)alkyl, (C$_5$-C$_7$)cycloalkyl, (C$_3$-C$_7$)cycloalkyl(C$_1$-C$_5$)alkyl, (C$_2$-C$_5$)alkenyl, halo(C$_2$-C$_5$)alkenyl, (C$_5$-C$_6$)cycloalkenyl, (C$_2$-C$_4$)alkynyl, phenyl, benzyl, phenethyl and substituted phenyl, benzyl or phenethyl, the aromatic portion of which may be substituted with 1 or 2 halo or trihalomethyl substituents, provided that when Z is phenyl, W is not NB$_2$ and when Z is methyl, W is not methoxy, and Q is 1-(1,2,4-triazolyl).

A more preferred embodiment of this invention is the compounds, enantiomorphs, salts and complexes of Formulas (I) and (II) wherein X is phenyl, optionally substituted at the 4-position with chloro, bromo, fluoro or trifluoromethyl; Z is $(C_1-C_6)$alkyl, $(C_5-C_6)$ cycloalkyl, phenyl, benzyl, phenethyl or monochloro substituted phenyl, benzyl or phenethyl, provided that when Z is phenyl, W is not $NB_2$ and when Z is methyl, W is not methoxy; and Q is 1-(1,2,4-triazolyl).

The compounds described and claimed herein were synthesized starting from the known arylcyanoalkyl-1,2,4-triazoles. The general steps are:

A. Hydrolysis of nitrile to acid;
B. Hydrolysis of nitrile to amide;
C. Hydrolysis of amide to acid;
D. Esterification of acid to ester;
D''. Esterification of acid chloride to ester;
E. Alkylation of amide to dialkylamide;
E''. Acid to acid chloride; amidation of acid chloride; and
L. Preparation of cyano ester.

These procedures apply to (2-carbonyl)ethyl-1,2,4-triazoles in which the aryl group, X, is either substituted or unsubstituted. The methods employed are well known and can be found in any standard treatise on synthetic chemistry, such as J. March. *Advanced Organic Chemistry-Reactions, Mechanism and Structure*, 3rd Edition, John Wiley & Sons, 1985, hereinafter "March". The reaction is outlined in Scheme 1.

In Scheme 1, X, Z and Q are as defined in formula I; and $W^1$ is R, R'OR'', R'Y, R'COOR'' and R'OCOR'' wherein R, $R^1$, R'' and Y are as defined in formula I. (In each instance where the term "phenyl" occurs in the description of the Steps of Scheme 1, it is to be considered representative of the substituent X where X is defined in formula I.)

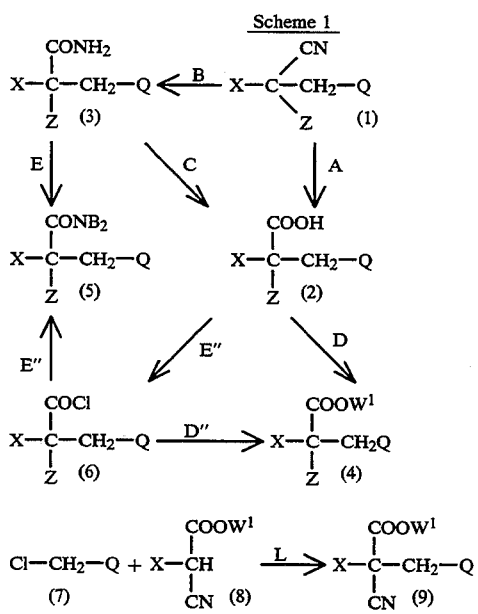

Scheme 1

Step A: Hydrolysis of Nitrile to Acid

The hydrolysis of a nitrile derivative (1) to a carboxylic acid (2) is performed under strongly acidic conditions using acids such as concentrated hydrochloric, 50-96% sulfuric, 48% hydrobromic; preferably, the hydrolysis is conducted at a temperature of about 100°-140° C. with 48% hydrobromic acid or concentrated hydrochloric acid for up to four days. Step A is preferred for phenyl derivatives which are not substituted in the ortho position.

Step B: Hydrolysis of Nitrile to Amide

The hydrolysis of a nitrile (1) to an amide (3) is conveniently effected with either a strong acid, such as used in Step A, or a strong base. When an acid is used, the hydrolysis is preferably conducted with 95% sulfuric acid at a temperature of about 80°-130° C., more preferably at a temperature of about 90°-110° C. for up to seven days.

Strongly basic conditions may be obtained by selecting a base such as concentrated sodium, potassium or lithium hydroxide. In addition to water, the hydrolysis may also be run in the presence of another solvent, for example a dipolar aprotic solvent such as dimethyl sulfoxide. Preferably, the hydrolysis is conducted with concentrated sodium hydroxide for about 1 to 3 hours. Generally, it is conducted at a temperature of about 80°-130° C., more preferably about 90°-110° C.

Step C: Hydrolysis of Amide to Acid

The amides (3) can be hydrolyzed to the corresponding carboxylic acids (2) directly using a strong acid such as those of Step A or to the salt of a carboxylic acid using a strong base such as those of Step B. Strong acids are preferred, preferably about 45-95% sulfuric or about 48% hydrobromic acid. The amide is reacted with the appropriate acid or base at a temperature of about 80°-160° C. and more preferably about 80°-130° C. This step is preferred for ortho-substituted phenyl derivatives.

Step D: Esterification of Acid to Ester

The esters (4) of this invention can be prepared using known techniques directly from the nitriles (1) using an alcohol and a strong acid catalyst or from the carboxylic acids (2) under milder reaction conditions, using an alcohol and strong acid with removal of the water formed. Alternatively, the sodium or potassium salt of the acid (2) can be formed under basic conditions using a base such as sodium hydride, potassium carbonate, or sodium or potassium hydroxide. The carboxylic acid salt preferably is reacted with an alkyl or aralkyl halide in a nucleophilic displacement type reaction to obtain the esters (4). A polar solvent, such as N,N-dimethylformamide (DMF) for a hydride base or methyl ethyl ketone (MEK) for a carbonate base, facilitates the reaction. Temperatures from room ambient temperature to about 110° C. may be utilized with reaction times up to one day.

Step D'': Esterification of Acid Chloride

Esters (4) can be prepared from the acid chloride (6) described in step E'' by the reaction with hydroxy derivatives such as alcohols, substituted phenols and hydroxy substituted heterocyles using a solvent such as tetrahydrofuran (THF), ether, methylene chloride and a basis catalyst such as pyridine or triethylamine at about 0°-50° C., preferably 10°-35° C., for up to 24 hours.

Step E: Alkylation of Amide to Dialkylamide

Primary amides (3) may be converted to N-substituted or N,N-disubstituted amides (5) by treatment with a strong base such as a hydride in the presence of a polar solvent such as DMF or dimethyl sulfoxide (DMSO). Preferably, sodium hydride in DMF solvent is employed to form the anion of the amide. The anionic intermediate is then reacted with either one or two equivalents of an alkyl or aryl halide, preferably a bromide or iodide, depending on whether the N-substituted or N,N-disubstituted amide is desired. Reaction temperatures from ambient room to about 100° C. may be employed with reaction times up to 24 hours.

Step E": Acid to Acid Chloride; Amidation of Acid Chloride

The N-substituted or N,N-disubstituted amides (5) can also be prepared from the carboxylic acids (2) via an acid chloride method. The acid chloride (6) can be prepared from the acid using standard chlorinating agents such as phosphorous pentachloride, phosphorous trichloride, phosphorous oxychloride, or preferably, thionyl chloride in a nonpolar solvent such as toluene at a temperature of about 0° C. to about 100° C. The acid chloride is best used immediately by reaction with a primary or secondary alkyl-, aralkyl-, or arylamine, or mixed amines, in a non-polar solvent such as methylene chloride or toluene at about 0°-50° C., preferably 10°-35° C., for up to about 24 hours.

Step L: Preparation of Cyanoesters

The cyanoesters can be prepared by first generating the salt of an alkyl arylcyano ester, such as ethyl phenylcyanoacetate, with a metal hydride, such as sodium hydride, in a dipolar aprotic solvent, such as DMF. The temperature may vary from about 10°-40° C., preferably 20°-30° C., with reaction times under 6 hours. After the salt of the ester has been prepared, a halomethyltriazole (7), preferably chloro- or bromomethyl-1,2,4-triazole, is reacted with the acid salt at about 20°-50° C. for up to 48 hours.

In an alternative synthesis (Scheme 2), certain 2-oxyphenyltriazole compounds may be prepared from 2-methoxyphenylcyanoalkyl-1,2,4-triazoles by hydrolysis (Step A') of the nitrile (11) with simultaneous removal of the methyl substituent to a lactone (12), lactone opening (Step D') to the di-sodium salt (13) and etherification and esterification (Step F'-1) to the ester (16), wherein R in OR and W¹ is the same moiety, optionally followed by hydrolysis (Step F'-2) to the acid (17) and alternate esterification (Step C') to the ester (15). The lactone (12) may also be converted (Step E'-1) to its potassium salt (14) and then etherified (Step E'-2) to give a new alkoxy compound (15), wherein R in OR and W¹ need not be the same moiety. Q, Z and R are as defined for Formula I. For the purposes of illustration, the aromatic ring is shown as an ortho-substituted phenyl ring.

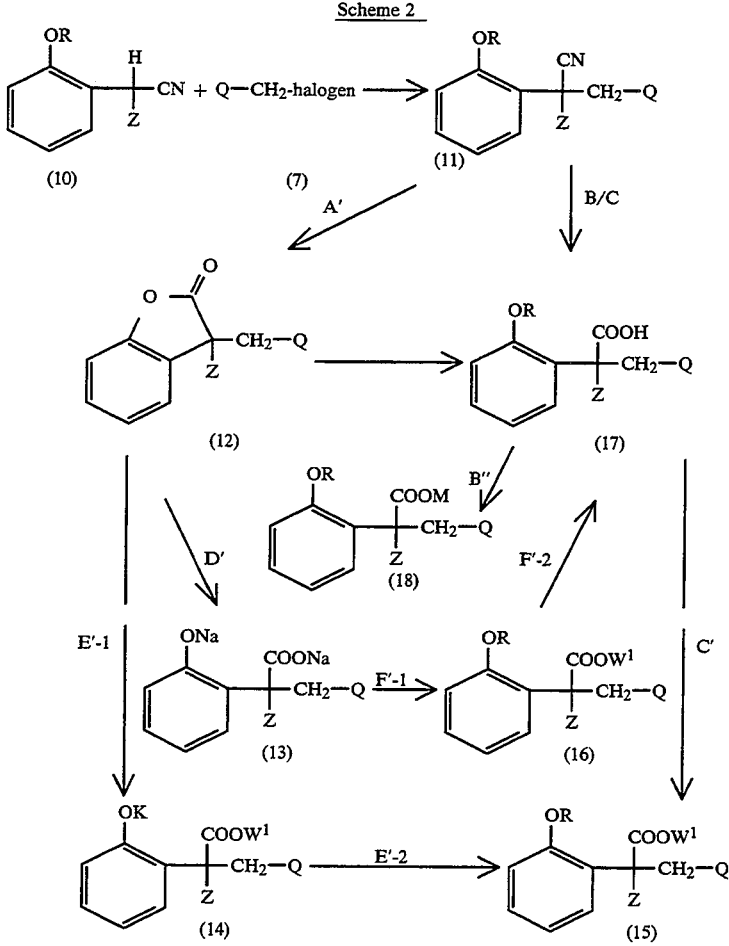

Scheme 2

When the substituent on the aryl is 2-methoxy, the more preferred route is as follows: A 2-methoxyaryl cyanide such as 2-methoxybenzyl cyanide, is reacted with an alkyl halide, such as cyclopentyl bromide or butyl bromide, or an aralkyl halide, such as benzyl bromide, in the presence of a strong base, such as sodium hydroxide, to form an alkylated or aralkylated intermediate (10). Reaction temperatures may be about 10°-50° C., preferably under 40° C. The reaction can generally be completed in less than 6 hours.

Triazoles (11) were synthesized according to the procedure of EP 251,775, which is herein incorporated by reference.

The purified intermediate (10) is dissolved in a dipolar aprotic solvent, such as DMF, and reacted with a strong base such as a metal hydride, preferably sodium hydride, to form an anion. Generally, ambient room temperature and a time period of under 2 hours is suitable. A solution of halomethyltriazole (7), preferably chloro- or bromomethyl-1,2,4-triazole, in a dipolar aprotic solvent, such as DMF, is added to the anionic alkylated intermediate (10) at a temperature of about 20°-60° C., preferably 25°-40° C., and allowed to react for a period of about 0.5-6.0 hours to form the triazole (11).

Step A': Nitrile Hydrolysis to Lactone

Lactones (12) are prepared by reacting a compound of Formula (11), such as α-benzyl-α-(2-methoxyphenyl)-1H-1,2,4-triazole-1-propane-nitrile, with a strong acid, such as hydrochloric, hydriodic, or hydrobromic, preferably 48% hydrobromic, at about 90°-120° C. for up to one week.

Step B': Lactone Opening to a Carboxylic Acid; Step B" to Form Salt

Carboxylic acid derivatives (17) can be prepared from lactones (12), such as 3-benzyl-3-[(1,2,4-triazol-1-yl)-methyl]-2(3H)-benzofuranone, by treating the lactone with an excess of basic alcohol solution, such as methanolic potassium hydroxide, for about 2-6 hours at a temperature from about 70°-120° C. After cooling, an alkyl halide, such as methyl iodide, is added and allowed to react at a temperature of from about 25°-70° C. for an additional time period of up to 6 hours.

An alkali metal, such as sodium or potassium, salt (18) of the carboxylic acid derivatives (17) can be prepared from (17) by the addition of the appropriate alkali metal hydroxide.

Step C': Esterification of Acid to Ester

This procedure is essentially identical to that described in Step D of the previous cascade.

Step D', F'-1: Lactone Opening Followed by Alkylation/Esterification

This method provides for identical alkoxy and ester groups and leads to compound (16).

Starting with lactones (12) in an alcoholic solvent such as methanol, the lactone is hydrolyzed by a strong base, such as 50% sodium hydroxide, to form a disalt intermediate (13). Temperatures of about 60°-110° C. are employed with reaction times up to 7 hours. After removal of the alcoholic solvent, a dipolar aprotic solvent such as DMF is added, followed by an alkyl, aralkyl or alkenyl halide, preferably a bromide or iodide. The reaction mixture is heated from about 35°-70° C. for up to 8 hours to yield an ester (16).

Step E'-1, E'-2: Lactone Opening to Phenoxide/Ester Followed by Alkylation

This method provides an alkoxy group different from the ester group by solvolysis of a lactone compound (12) to a phenoxide ester (14) using an alkoxide metal salt, such as potassium butoxide. The reaction is relatively facile and can be completed in the presence of a dipolar aprotic solvent, such as DMF, usually in under one hour at ambient temperature. An alkyl halide, such as methyl iodide, can then be added to the intermediate (14) and reacted at temperatures of about 20°-60° C. for about 0.5-4 hours to afford compound (15).

Step F'-2: Hydrolysis of Ester to Carboxylic Acid

Esters of Formula (16) may be hydrolyzed with either strong acids or bases in appropriate solvents. A strong base, such as 50% sodium hydroxide, in a dipolar aprotic solvent, such as dimethyl sulfoxide, may be employed. The ester in an aqueous dimethyl sulfoxide solvent is heated with the strong base at a temperature of about 80°-130° C. for up to 24 hours to afford compounds of formula (17).

The acid addition salts of the 1,2,4-triazoles of this invention can be prepared by standard techniques well-known in the art. For example, the 1,2,4-triazole of Formula (I) can be dissolved in an appropriate solvent such as diethyl ether, tetrahydrofuran, ethanol, methanol, and the like or combinations thereof, and treated with an equivalent or excess amount of a mineral or organic acid which may or may not be dissolved in an appropriate solvent. The mixture is then either cooled or evaporated to give the salt which can either be used as such or recrystallized from an appropriate solvent or combination of appropriate solvents.

The metal salt complexes of the above 1,2,4-triazoles can be prepared by adding dropwise, with stirring, a stoichiometric amount of a metal salt dissolved in an appropriate solvent or combination of solvents. The reaction mixture is briefly stirred and the solvent is removed under reduced pressure to give the metal salt complex of the 1,2,4-triazoles of Formula (II).

The metal salt complexes can also be prepared by mixing stoichiometric or excess amounts of the metal salt and a triazole of Formula (I) in the desired amount of solvent containing the appropriate adjuvants just prior to spraying the plants. Adjuvants that may be included in this in-situ preparation may be detergents, emulsifiers, wetting agents, spreading agents, dispersing agents, stickers, adhesives, and the like which are used in agricultural applications.

Solvents that can be utilized in these procedures include any polar solvent, for example, water, methanol, ethanol, isopropanol or ethylene glycol and any aprotic dipolar solvent, for example, dimethyl sulfoxide, acetonitrile, dimethylformamide, nitromethane or acetone.

The metal salt cations that can be used in these procedures can be selected from the group consisting of calcium, magnesium, manganese, copper, nickel, zinc, iron, cobalt, tin, cadmium, mercury, chromium, lead, barium and the like.

Anions such as chloride, bromide, iodide, sulfate, bisulfate, phosphate, nitrate, perchlorate, carbonate, bicarbonate, hydrosulfide, hydroxide, acetate, oxalate, malate, citrate and the like may be utilized as the counterion in the metal salt.

The compounds of this invention possess an asymmetric carbon atom and thus exist as racemic mixtures. The d and l enantiomorphs in these racemic mixtures can be separated via standard techniques such as fractional crystallization with d-tartaric acid, l -tartaric acid, l-quinic acid and the like followed by basification and extraction of the d or l enantiomorph free base.

Table 1 lists certain compounds of the invention, along with their melting points. Elemental analyses are given in Table 2 for some of the compounds.

TABLE 1

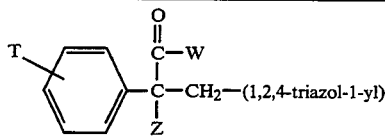

| No. | Method | T | Z | W | Melting Point (°C.) |
|---|---|---|---|---|---|
| 1 | C | 4CL | $C_2H_5$ | OH | 182–184 |
| 2 | D | 4CL | $C_2H_5$ | $OCH_3$ | OIL |
| 3 | D | CL | $C_2H_5$ | $OC_3H_5$ | OIL |
| 4 | D | 4CL | $C_2H_5$ | $OC_3H_7$ | OIL |
| 5 | C | 2,4CL | $C_2H_5$ | OH | 206–208 |
| 6 | B' | $2OCH_3$ | $n$-$C_3H_7$ | OH | 195–196 |
| 7 | B'' | $2OCH_3$ | $n$-$C_3H_7$ | OK | 150–152 |
| 8 | D'/F'-1 | $2OCH_3$ | $n$-$C_3H_7$ | $OCH_3$ | 105–106 |
| 9 | D'/F'-1 | $2OC_4H_9$ | $n$-$C_3H_7$ | $OC_4H_9$ | OIL |
| 10 | D'/F'-1 | $2OCH_2CH_2OCH_3$ | $n$-$C_3H_7$ | $OCH_2CH_2OCH_3$ | OIL |
| 11 | A' | LACTONE | $n$-$C_3H_7$ | LACTONE | 140–141 |
| 12 | A | H | $n$-$C_4H_9$ | OH | 181–183 |
| 13 | D | H | $n$-$C_4H_9$ | $OCH_3$ | OIL |
| 14 | D | H | $n$-$C_4H_9$ | $O(i$-$C_3H_7)$ | OIL |
| 15 | D | H | $n$-$C_4H_9$ | $OCH_2CH_2OCH_3$ | OIL |
| 16 | A | 4CL | $n$-$C_4H_9$ | OH | 169–171 |
| 17 | D | 4CL | $n$-$C_4H_9$ | $OCH_3$ | 78–80 |
| 18 | D | 4CL | $n$-$C_4H_9$ | $OCH_2CH_3$ | OIL |
| 19 | D | 4CL | $n$-$C_4H_9$ | $OC_3H_7$ | 52–56 |
| 20 | D | 4CL | $n$-$C_4H_9$ | $OC_4H_9$ | OIL |
| 21 | D | 4CL | $n$-$C_4H_9$ | $OCH_2C_6H_5$ | OIL |
| 22 | D | 4CL | $n$-$C_4H_9$ | $OCH_2CO_2CH_3$ | OIL |
| 23 | D | 4CL | $n$-$C_4H_9$ | $OCH_2CO_2C_2H_5$ | OIL |
| 24 | D | 4CL | $n$-$C_4H_9$ | $OCH_2CO_2C(CH_3)_3$ | OIL |
| 25 | D | 4CL | $n$-$C_4H_9$ | $OCH_2CH=CH_2$ | 61–62 |
| 26 | D | 4CL | $n$-$C_4H_9$ | $OCH_2C\equiv CH$ | 67–69 |
| 27 | D | 4CL | $n$-$C_4H_9$ | $OCH_2CH_2C_6H_4(4CL)$ | OIL |
| 28 | D | 4CL | $n$-$C_4H_9$ | $OCH_2(3Pyridyl)$ | OIL |
| 29 | D | 4CL | $n$-$C_4H_9$ | $OCH_2(4Pyridyl)$ | OIL |
| 30 | D | 4CL | $n$-$C_4H_9$ | $OCH_2OCOC(CH_3)_3$ | 84–86 |
| 31 | D | 4CL | $n$-$C_4H_9$ | $OCH_2CH=CHCO_2CH_3$ | OIL |
| 32 | D | 4CL | $n$-$C_4H_9$ | $OCH_2OCH_2C_6H_5$ | OIL |
| 33 | D | 4CL | $n$-$C_4H_9$ | $OCH_2OCH_2CH_2Si(CH_3)_3$ | OIL |
| 34 | D | 4CL | $n$-$C_4H_9$ | $OCH_2$Phthalimide | 122–124 |
| 35 | D | 4CL | $n$-$C_4H_9$ | $O(CH_2)_2$Phthalimide | 119–120 |
| 36 | D | 4CL | $n$-$C_4H_9$ | $O(CH_2)_2$Morpholine | OIL |
| 37 | D | 4CL | $n$-$C_4H_9$ | $OCH_2CH=CHC_6H_5$ | OIL |
| 38 | D | 4CL | $n$-$C_4H_9$ | $OCH_2(1H$-$1,2,4$-Triazole) | 109–111 |
| 39 | C | 2,4CL | $n$-$C_4H_9$ | OH | 207–210 |
| 40 | D | 2,4CL | $n$-$C_4H_9$ | $OCH_3$ | OIL |
| 41 | D | 2,4CL | $n$-$C_4H_9$ | $OC_2H_5$ | OIL |
| 42 | D | 2,4CL | $n$-$C_4H_9$ | $OC_3H_7$ | OIL |
| 43 | D | 2,4CL | $n$-$C_4H_9$ | $O(i$-$C_3H_7)$ | 100–101 |
| 44 | D | 2,4CL | $n$-$C_4H_9$ | $OC_4H_9$ | OIL |
| 45 | D | 2,4CL | $n$-$C_4H_9$ | $O(i$-$C_4H_9)$ | OIL |
| 46 | D | 2,4CL | $n$-$C_4H_9$ | $OC_8H_{17}$ | OIL |
| 47 | D | 2,4CL | $n$-$C_4H_9$ | $OCH_2C_6H_5$ | OIL |
| 48 | D | 2,4CL | $n$-$C_4H_9$ | $OCH_2CH_2OH$ | 135–137 |
| 49 | D | 2,4CL | $n$-$C_4H_9$ | $OCH_2CH(OH)CH_3$ | OIL |
| 50 | D | 2,4CL | $n$-$C_4H_9$ | $OCH_2OCH_3$ | OIL |
| 51 | D | 2,4CL | $n$-$C_4H_9$ | $OCH_2CH_2OCH_3$ | OIL |
| 52 | D | 2,4CL | $n$-$C_4H_9$ | $OCH(OCH_2CH_3)CH_3$ | OIL |
| 53 | D | 2,4CL | $n$-$C_4H_9$ | $OCH(CN)CH_3$ | OIL |
| 54 | D | 2,4CL | $n$-$C_4H_9$ | $OCH_2CO_2CH_3$ | 95–96 |
| 55 | D | 2,4CL | $n$-$C_4H_9$ | $OCH(CH_3)CO_2CH_3$ | OIL |
| 56 | D | 2,4CL | $n$-$C_4H_9$ | $OCH_2CH_2OCOCH_3$ | OIL |
| 57 | D | 2,4CL | $n$-$C_4H_9$ | $OCH_2C\equiv CH$ | OIL |
| 58 | D | 2,4CL | $n$-$C_4H_9$ | $OCH_2C(CL)=CH_2$ | OIL |
| 59 | F'-1/F'-2 | $2OCH_3$ | $n$-$C_4H_9$ | OH | 198 |
| 60 | B'' | $2OCH_3$ | $n$-$C_4H_9$ | OK | 160–170 |
| 61 | D'/F''-1 | $2OCH_3$ | $n$-$C_4H_9$ | $OCH_3$ | 132 |
| 62 | C' | $2OCH_3$ | $n$-$C_4H_9$ | $OC_2H_5$ | RESIN |
| 63 | C' | $2OCH_3$ | $n$-$C_4H_9$ | $OCH_2CF_3$ | 65–68 |
| 64 | D | $2OCH_3$ | $n$-$C_4H_9$ | $O(i$-$C_3H_7)$ | OIL |
| 65 | D | $2OCH_3$ | $n$-$C_4H_9$ | $OCH_2OCH_3$ | OIL |
| 66 | D | $2OCH_3$ | $n$-$C_4H_9$ | $OCH_2CH_2OCH_3$ | OIL |
| 67 | D | $2OCH_3$ | $n$-$C_4H_9$ | $OCH_2CH_2OC_2H_5$ | OIL |
| 68 | D | $2OCH_3$ | $n$-$C_4H_9$ | $OCH(CH_3)CN$ | OIL |
| 69 | E'-1/E'-2 | $2OCH_3$ | $n$-$C_4H_9$ | $OC(CH_3)_3$ | OIL |
| 70 | C' | $2OCH_3$ | $n$-$C_4H_9$ | $OCH_2$OXIRANE | OIL |
| 71 | A' | LACTONE | $n$-$C_4H_9$ | LACTONE | 90–91 |
| 72 | D'/F''-1 | $2OC_2H_5$ | $n$-$C_4H_9$ | $OC_2H_5$ | OIL |

TABLE 1-continued

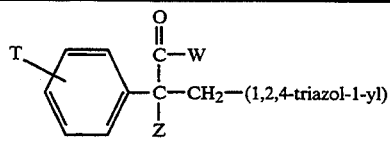

—CH₂—(1,2,4-triazol-1-yl)

| No. | Method | T | Z | W | Melting Point (°C.) |
|---|---|---|---|---|---|
| 73 | E'-1/E'-2 | 2OC₂H₅ | n-C₄H₉ | OC(CH₃)₃ | OIL |
| 74 | D'/F'-1 | 2OC₃H₇ | n-C₄H₉ | OC₃H₇ | OIL |
| 75 | E'-1/E'-2 | 2OC₃H₇ | n-C₄H₉ | OC(CH₃)₃ | OIL |
| 76 | D'/F'-1 | 2O(i-C₃H₇) | n-C₄H₉ | O(i-C₃H₇) | 70-72 |
| 77 | E'-1/E'-2 | 2OC₄H₉ | n-C₄H₉ | OC(CH₃)₃ | OIL |
| 78 | D'/F'-1 | 2OCH₂C≡CH | n-C₄H₉ | OCH₂C≡CH | 110-112 |
| 79 | D'/F'-1 | 2OCH₂CH₂OCH₃ | n-C₄H₉ | OCH₂CH₂OCH₃ | OIL |
| 80 | A | 4F | i-C₅H₁₁ | OH | 187-190 |
| 81 | D | 4F | i-C₅H₁₁ | OC₃H₇ | OIL |
| 82 | D | 4F | i-C₅H₁₁ | OCH₂CH₂OCH₃ | OIL |
| 83 | A' | LACTONE | c-C₅H₉ | LACTONE | 135-136 |
| 84 | B' | 2OCH₃ | c-C₅H₉ | OH | >300 |
| 85 | B'' | 2OCH₃ | c-C₅H₉ | OK | 297-300 |
| 86 | D'/F'-1 | 2OCH₃ | c-C₅H₉ | OCH₃ | RESIN |
| 87 | A' | LACTONE | c-C₆H₁₁ | LACTONE | 198-200 |
| 88 | D'/F'-1 | 2OCH₃ | c-C₆H₁₁ | OCH₃ | RESIN |
| 89 | C | 2,4CL | CH₂C₆H₅ | OH | 220-222 |
| 90 | D | 2,4CL | CH₂C₆H₅ | O(i-C₃H₇) | 124-125 |
| 91 | D | 2,4CL | CH₂C₆H₅ | OCH₂CH₂OCH₃ | 148-150 |
| 92 | C | 2F | CH₂C₆H₅ | OH | 227-230 |
| 93 | D | 2F | CH₂C₆H₅ | OC₂H₅ | OIL |
| 94 | A' | LACTONE | CH₂C₆H₅ | LACTONE | 150 |
| 95 | B | 2OCH₃ | CH₂C₆H₅ | OH | 250-2521 |
| 96 | B | 2OCH₃ | CH₂C₆H₅ | OK | 270-273 |
| 97 | D'/F'-1 | 2OCH₃ | CH₂C₆H₅ | OCH₃ | 97 |
| 98 | C' | 2OCH₃ | CH₂C₆H₅ | OC₂H₅ | OIL |
| 99 | C' | 2OCH₃ | CH₂C₆H₅ | OCH₂CF₃ | RESIN |
| 100 | C' | 2OCH₃ | CH₂C₆H₅ | OC₃H₇ | 129-130 |
| 101 | C' | 2OCH₃ | CH₂C₆H₅ | OCH₂CH₂OCH₃ | OIL |
| 102 | C | 4OCH₃ | CH₂C₆H₅ | OH | 206-207 |
| 103 | D | 4OCH₃ | CH₂C₆H₅ | OC₃H₇ | OIL |
| 104 | D | 4OCH₃ | CH₂C₆H₅ | OCH₂CH₂OCH₃ | OIL |
| 105 | C' | 2OC₂H₅ | CH₂C₆H₅ | OCH₃ | OIL |
| 106 | D'/F'-1 | 2OC₂H₅ | CH₂C₆H₅ | OC₂H₅ | OIL |
| 107 | C' | 2OC₂H₅ | CH₂C₆H₅ | OC₃H₇ | OIL |
| 108 | C' | 2OC₂H₅ | CH₂C₆H₅ | O(i-C₃H₇) | OIL |
| 109 | C' | 2OC₂H₅ | CH₂C₆H₅ | OCH₂CH₂OCH₃ | OIL |
| 110 | C' | 2OC₂H₅ | CH₂C₆H₅ | OC₄H₉ | OIL |
| 111 | C' | 2OC₂H₅ | CH₂C₆H₅ | O(i-C₄H₉) | Semi-Solid |
| 112 | E'-1/E'-2 | 2OC₂H₅ | CH₂C₆H₅ | OC(CH₃)₃ | Semi-Solid |
| 113 | D'/F'-1 | 2OC₃H₇ | CH₂C₆H₅ | OC₃H₇ | OIL |
| 114 | D'/F'-1 | 2O(i-C₃H₇) | CH₂C₆H₅ | O(i-C₃H₇) | OIL |
| 115 | D'/F'-1 | 2OC₄H₉ | CH₂C₆H₅ | OC₄H₉ | OIL |
| 116 | D'/F'-1 | 2OCH₂CH=CH₂ | CH₂C₆H₅ | OCH₂CH=CH₂ | OIL |
| 117 | D'/F'-1 | 2OCH₂CH₂OCH₃ | CH₂C₆H₅ | OCH₂CH₂OCH₃ | OIL |
| 118 | A' | LACTONE | CH₂C₆H₄(2CL) | LACTONE | 142 |
| 119 | D'/F'-1 | 2OCH₃ | CH₂C₆H₄(2CL) | OCH₃ | 144-145 |
| 120 | C' | 2OCH₃ | CH₂C₆H₄(2CL) | OC₂H₅ | OIL |
| 121 | C' | 2OCH₃ | CH₂C₆H₄(2CL) | O(i-C₃H₇) | 124-125 |
| 122 | D'/F'-1 | 2OC₂H₅ | CH₂C₆H₄(2CL) | OC₂H₅ | OIL |
| 123 | C | 2OCH₃ | CH₂C₆H₄(4CF₃) | OH | GLASS |
| 124 | D | 2OCH₃ | CH₂C₆H₄(4CF₃) | OCH₂CH₂OCH₂CH₃ | OIL |
| 125 | D | 2OCH₃ | CH₂C₆H₄(4CH₃) | O(i-C₃H₇) | OIL |
| 126 | C | H | CH₂CH₂C₆H₄(4CL) | OH | 188-190 |
| 127 | D | H | CH₂CH₂C₆H₄(4CL) | OCH₃ | 115-117 |
| 128 | D | H | CH₂CH₂C₆H₄(4CL) | OC₂H₅ | 95-97 |
| 129 | D | H | CH₂CH₂C₆H₄(4CL) | OC₃H₇ | 73-74 |
| 130 | D | H | CH₂CH₂C₆H₄(4CL) | O(i-C₃H₇) | 90-92 |
| 131 | D | H | CH₂CH₂C₆H₄(4CL) | OC₄H₉ | RESIN |
| 132 | D | H | CH₂CH₂C₆H₄(4CL) | O(i-C₄H₉) | 65-67 |
| 133 | D | H | CH₂CH₂C₆H₄(4CL) | O(i-C₅H₁₁) | 101-102 |
| 134 | D | H | CH₂CH₂C₆H₄(4CL) | OC₈H₁₇ | OIL |
| 135 | D | H | CH₂CH₂C₆H₄(4CL) | OCH₂C₆H₅ | 102-103 |
| 136 | D | H | CH₂CH₂C₆H₄(4CL) | OCH₂CH₂C₆H₅ | 80-81 |
| 137 | D | H | CH₂CH₂C₆H₄(4CL) | OCH₂CH=CH₂ | 83-84 |
| 138 | D | H | CH₂CH₂C₆H₄(4CL) | OCH₂C≡CH | 79-80 |
| 139 | D | H | CH₂CH₂C₆H₄(4CL) | OCH₂OCH₃ | OIL |
| 140 | D | H | CH₂CH₂C₆H₄(4CL) | OCH₂CH₂OCH₃ | OIL |
| 141 | D | H | CH₂CH₂C₆H₄(4CL) | OCH₂CH₂OCH₂CH₃ | OIL |
| 142 | D | H | CH₂CH₂C₆H₄(4CL) | OCH₂OCH₂C₆H₅ | OIL |
| 143 | D | H | CH₂CH₂C₆H₄(4CL) | OCH₂CO₂CH₃ | OIL |
| 144 | D | H | CH₂CH₂C₆H₄(4CL) | OCH₂CH=CHCO₂CH₃ | OIL |

TABLE 1-continued

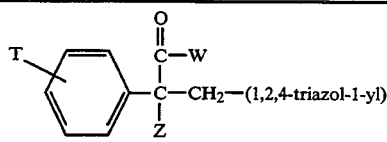

| No. | Method | T | Z | W | Melting Point (°C.) |
|---|---|---|---|---|---|
| 145 | A' | LACTONE | $CH_2CH_2C_6H_4(4CL)$ | LACTONE | 155–156 |
| 146 | C | $2OCH_3$ | $CH_2CH_2C_6H_4(4CL)$ | OH | RESIN |
| 147 | D'/F'-1 | $2OCH_3$ | $CH_2CH_2C_6H_4(4CL)$ | $OCH_3$ | RESIN |
| 148 | D | $2OCH_3$ | $CH_2CH_2C_6H_4(4CL)$ | $OC_3H_7$ | OIL |
| 149 | D | $2OCH_3$ | $CH_2CH_2C_6H_4(4CL)$ | $OCH_2CH_2OCH_3$ | OIL |
| 150 | C | 3CL | $CH_2CH_2C_6H_4(4F)$ | OH | 138–140 |
| 151 | D | 2,4CL | $CH_2CH_2C_6H_4(4F)$ | $OC_3H_7$ | OIL |
| 152 | D | 3CL | $CH_2CH_2C_6H_4(4F)$ | $OCH_2CH_2OCH_3$ | OIL |
| 153 | B | 4CL | $C_2H_5$ | $NH_2$ | 139–141 |
| 154 | B | 2,4CL | $C_2H_5$ | $NH_2$ | 164–165 |
| 155 | B | H | $n\text{-}C_4H_9$ | $NH_2$ | 140–142 |
| 156 | E" | H | $n\text{-}C_4H_9$ | (3,5Piperidin-1-yl) | 120–122 |
| 157 | B | 4CL | $n\text{-}C_4H_9$ | $NH_2$ | 197–199 |
| 158 | E | 4CL | $n\text{-}C_4H_9$ | $NHC_3H_7$ | 107–110 |
| 159 | E | 4CL | $n\text{-}C_4H_9$ | $NHC_4H_9$ | 109–111 |
| 160 | E | 4CL | $n\text{-}C_4H_9$ | $N(CH_3)_2$ | OIL |
| 161 | E | 4CL | $n\text{-}C_4H_9$ | $N(C_2H_5)_2$ | OIL |
| 162 | B | 2,4CL | $n\text{-}C_4H_9$ | $NH_2$ | 170–172 |
| 163 | E" | 2,4CL | $n\text{-}C_4H_9$ | $NH(i\text{-}C_3H_7)$ | 158–160 |
| 164 | E" | 2,4CL | $n\text{-}C_4H_9$ | $NH(i\text{-}C_5H_{11})$ | 172–173 |
| 165 | E" | 2,4CL | $n\text{-}C_4H_9$ | 4-Morpholinyl | 225–227 |
| 166 | B | $2OCH_3$ | $n\text{-}C_4H_9$ | $NH_2$ | 155–156 |
| 167 | B | 2,4CL | $CH_2C_6H_5$ | $NH_2$ | 218–220 |
| 168 | B | 2F | $CH_2C_6H_5$ | $NH_2$ | 165–167 |
| 169 | B | $2OCH_3$ | $CH_2C_6H_5$ | $NH_2$ | 175–178 |
| 170 | B | H | $CH_2CH_2C_6H_4(4CL)$ | $NH_2$ | 169–171 |
| 171 | D | 2,4CL | $C_2H_5$ | $OC_3H_7$ | 99–101 |
| 172 | D | 2,4CL | $C_2H_5$ | $OC_4H_9$ | OIL |
| 173 | D | 2,4CL | $C_2H_5$ | $OC_6H_{13}$ | OIL |
| 174 | D | 4CL | $C_2H_5$ | $OC_4H_9$ | OIL |
| 175 | D | 4CL | $C_2H_5$ | $OC_6H_{13}$ | OIL |
| 176 | D | 4CL | $C_2H_5$ | $OC_{10}H_{21}$ | OIL |
| 177 | D | 4CL | $C_2H_5$ | $OCH_2C_6H_5$ | OIL |
| 178 | L | H | CN | $OC_2H_5$ | OIL |
| 179A | E" | H | $CH_2CH_2C_6H_4(4CL)$ | (R)-$NHCH(CH_2OH)C_2H_5$ | OIL |
| 179B | E" | H | $CH_2CH_2C_6H_4(4CL)$ | (S)-$NHCH(CH_2OH)C_2H_5$ | OIL |

The designation "lactone" refers to a compound prepared by Method A' of general structure:

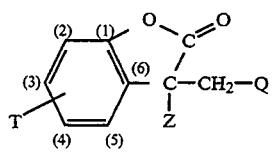

TABLE 2

| Ex. No. | Analysis | Carbon | Hydrogen | Nitrogen | Oxygen | Chlorine | Silicon | Fluorine |
|---|---|---|---|---|---|---|---|---|
| 2 | Calculated | 57.22 | 5.49 | 14.31 | 10.89 | 12.08 | | |
|   | Found | 56.60 | 5.65 | 13.59 | 10.88 | 11.27 | | |
| 3 | Calculated | 58.51 | 5.89 | 13.69 | 10.40 | 11.52 | | |
|   | Found | 58.18 | 6.07 | 13.34 | 10.15 | 11.12 | | |
| 4 | Calculated | 59.69 | 6.26 | 13.06 | 9.95 | 11.02 | | |
|   | Found | 58.56 | 6.51 | 12.68 | 9.96 | 10.60 | | |
| 13 | Calculated | 66.85 | 7.37 | 14.63 | 11.14 | | | |
|   | Found | 67.31 | 7.38 | 14.07 | 11.12 | | | |
| 18 | Calculated | 60.27 | 6.60 | 12.52 | 9.53 | 11.08 | | |
|   | Found | 60.78 | 6.55 | 12.53 | 9.00 | 10.58 | | |
| 20 | Calculated | 62.69 | 7.20 | 11.55 | 8.80 | 9.77 | | |
|   | Found | 62.77 | 7.23 | 12.17 | 8.80 | 9.79 | | |
| 21 | Calculated | 66.38 | 6.08 | 10.56 | 8.04 | 8.94 | | |
|   | Found | 66.70 | 6.55 | 10.04 | 8.10 | 8.72 | | |
| 22 | Calculated | 56.89 | 5.84 | 11.07 | 16.86 | 9.34 | | |
|   | Found | 56.69 | 5.88 | 11.03 | 16.91 | 9.28 | | |
| 23 | Calculated | 57.92 | 6.14 | 10.68 | 16.26 | 9.00 | | |
|   | Found | 57.94 | 6.18 | 10.79 | 16.34 | 8.79 | | |
| 24 | Calculated | 58.58 | 6.89 | 10.26 | 15.62 | 8.65 | | |
|   | Found | 59.58 | 6.85 | 9.88 | 15.63 | 8.39 | | |

TABLE 2-continued

Elemental Analysis

| Ex. No. | Analysis | Carbon | Hydrogen | Nitrogen | Oxygen | Chlorine | Silicon | Fluorine |
|---|---|---|---|---|---|---|---|---|
| 27 | Calculated | 61.87 | 5.65 | 9.42 | 7.17 | 15.89 | | |
|  | Found | 61.11 | 5.92 | 9.04 | 8.39 | 15.39 | | |
| 28 | Calculated | 63.21 | 5.81 | 14.05 | 8.03 | 8.89 | | |
|  | Found | 63.07 | 5.70 | 13.70 | 8.23 | 9.07 | | |
| 29 | Calculated | 63.21 | 5.81 | 14.05 | 8.03 | 8.89 | | |
|  | Found | 62.42 | 5.93 | 13.70 | 9.27 | 8.56 | | |
| 31 | Calculated | 62.77 | 6.92 | 12.02 | 9.15 | 10.14 | | |
|  | Founci | 61.70 | 6.80 | 12.20 | 8.94 | 10.42 | | |
| 32 | Calculated | 64.53 | 6.13 | 9.83 | 11.79 | 8.29 | | |
|  | Found | 64.03 | 6.12 | 9.44 | 12.19 | 8.34 | | |
| 33 | Calculated | 59.75 | 7.65 | 9.96 | 7.59 | 8.41 | 6.65 | 14.62 |
|  | Found | 58.32 | 7.72 | 10.11 | 7.73 | 8.15 | 6.85 | 12.79 |
| 36 | Calculated | 59.90 | 6.95 | 13.32 | 11.41 | 8.43 | | |
|  | Found | 59.58 | 7.01 | 12.87 | 11.98 | 8.42 | | |
| 37 | Calculated | 67.98 | 6.18 | 9.92 | 7.55 | 3.37 | | |
|  | Found | 68.11 | 6.29 | 9.36 | 7.64 | 8.40 | | |
| 40 | Calculated | 54.07 | 5.10 | 11.83 | 9.01 | 19.97 | | |
|  | Found | 54.40 | 5.54 | 11.60 | 8.38 | 19.73 | | |
| 41 | Calculated | 55.12 | 5.72 | 11.36 | 8.65 | 19.16 | | |
|  | Found | 55.19 | 5.86 | 11.42 | 8.92 | 19.09 | | |
| 42 | Calculated | 56.23 | 6.03 | 10.94 | 8.33 | 18.46 | | |
|  | Found | 57.03 | 6.33 | 10.97 | 8.06 | 17.26 | | |
| 46 | Calculated | 60.76 | 7.33 | 9.35 | 7.04 | 15.62 | | |
|  | Found | 60.85 | 7.50 | 10.79 | 6.03 | 15.26 | | |
| 131 | Calculated | 67.04 | 6.37 | 10.21 | 7.77 | 8.62 | | |
|  | Found | 67.19 | 6.57 | 10.44 | 7.73 | 8.71 | | |
| 134 | Calculated | 69.27 | 7.32 | 8.98 | 6.84 | 7.58 | | |
|  | Found | 68.41 | 7.34 | 8.91 | 6.54 | 9.04 | | |
| 139 | Calculated | 63.06 | 5.55 | 10.52 | 12.01 | 8.87 | | |
|  | Found | 62.17 | 5.65 | 9.25 | 13.77 | 7.75 | | |
| 140 | Calculated | 63.82 | 5.84 | 10.16 | 11.60 | 8.57 | | |
|  | Found | 63.56 | 5.77 | 10.22 | 11.76 | 8.74 | | |
| 141 | Calculated | 64.54 | 6.13 | 9.83 | 11.22 | 8.29 | | |
|  | Found | 64.23 | 6.08 | 10.08 | 11.51 | 8.39 | | |
| 142 | Calculated | 68.11 | 5.50 | 8.83 | 10.09 | 7.45 | | |
|  | Found | 65.77 | 5.44 | 8.20 | 11.96 | 7.29 | | |
| 143 | Calculated | 61.73 | 5.19 | 9.83 | 14.97 | 8.29 | | |
|  | Found | 62.19 | 5.31 | 10.23 | 14.11 | 7.97 | | |
| 144 | Calculated | 63.48 | 5.33 | 9.26 | 14.11 | 7.81 | | |
|  | Found | 60.58 | 5.33 | 8.81 | 14.64 | 7.53 | | |
| 160 | Calculated | 60.95 | 6.92 | 16.74 | 4.78 | 10.59 | | |
|  | Found | 60.57 | 6.96 | 16.38 | 5.82 | 10.55 | | |
| 161 | Calculated | 62.86 | 7.50 | 15.44 | 4.41 | 9.77 | | |
|  | Found | 63.19 | 7.15 | 15.39 | 4.55 | 9.67 | | |
| 172 | Calculated | 55.12 | 5.72 | 11.35 | 8.65 | 19.16 | | |
|  | Found | 55.44 | 5.84 | 11.52 | 8.61 | 18.66 | | |
| 173 | Calculated | 57.27 | 6.33 | 10.55 | 8.04 | 17.81 | | |
|  | Found | 57.53 | 6.41 | 10.61 | 8.40 | 17.38 | | |
| 174 | Calculated | 60.78 | 6.61 | 12.52 | 9.53 | 10.56 | | |
|  | Found | 60.77 | 6.63 | 12.44 | 9.85 | 10.43 | | |
| 175 | Calculated | 62.69 | 7.21 | 11.55 | 8.80 | 9.75 | | |
|  | Found | 62.58 | 7.11 | 11.59 | 8.54 | 10.03 | | |
| 176 | Calculated | 65.75 | 8.16 | 10.01 | 7.62 | 8.44 | | |
|  | Found | 65.24 | 7.96 | 9.05 | 7.90 | 8.62 | | |
| 177 | Calculated | 64.92 | 5.45 | 11.37 | 8.65 | 9.51 | | |
|  | Found | 65.01 | 5.66 | 11.10 | 8.75 | 9.45 | | |
| 178 | Calculated | 62.19 | 5.22 | 20.74 | 11.84 | | | |
|  | Found | 61.95 | 5.27 | 20.70 | 11.68 | | | |

Table 3-NMR shifts for Examples of the Invention

EX. No. 5
NMR: 200 MHz (d$_6$-DMSO): 1.0–1.1(t,3H),1.9–2.3(m,2H),3.1–3.5(br s,1H),4.7–5.1(ABq,2H), 7.0–7.1(d,1H),7.30–7.35(dd,1H),7.65–7.70(d,1H), 7.8(s,1H), and 8.0(s,1H).

EX. No. 6
NMR: 200 MHz (d$_6$-DMSO): 1.0–2.3(m,7H),3.8(s,3H),4.5–4.9(ABq,2H)6.8–7.3(m,4H),7.5(br s,1H) and 7.9(br s,1H).

EX. No. 7
NMR: 200 MHz (d$_6$-DMSO) 0.9–1.7(m,5H),2.5–3.2(ABq,2H),3.8(br s,3H),4.6–4.8(ABq,2H), 6.7–7.4(m,4H),7.8(br s,1H) and 8.4(br s,1H).

EX. No. 8
NMR: 200 MHz (CDCl$_3$): 0.9–1.1(t,3H), 1.2–1.4(m,1H), 1.7–2.0(m,3H), 3.7(s,3H),3.8(s,3H), 4.8(s,2H),6.7–7.0(m,3H),7.0–7.1(br s,1H), 7.2–7.3(m,1H) and 7.7–7.8(br s,1H).

EX. No. 9
NMR: 200 MHz (CDCl$_3$): 0.8–0.9(t,3H),0.9–1.0(t,6H),1.2–1.4(m,4H),1.4–1.7(m,4H), 1.7–1.9(m,4H),3.9–4.2(m,4H),4.8(s,2H),6.7–7.2(m,5H) and 7.8(s,1H).

EX. No. 10
NMR: 200 MHz (CDCl$_3$): 1.0–1.1(t,3H),1.2–1.4(m,1H),1.7–2.1(m,5H),3.3(s,3H),3.4(s,3H), 3.5–3.6(t,2H),3.7–3.8(t,2H),4.1–4.4(m,4H), 4.7–5.0(ABq,2H),6.7–7.2(m,4H),7.1(s,1H) and 7.8(s,1H).

EX. No. 11

NMR: 200 MHz (CDCl₃): 1.0–1.1(t,3H),1.2–1.4(m,1H),1.7–2.1(m,5H),3.3(s,3H),3.4H), 3.5–3.6(t,2H),3.7–3.8(t,2H),4.1–4.4(m,4H), 4.7–5.0(ABq,2H),6.7–7.2(m,4H),7.1(s,1H) and 7.8(s,1H).

EX. No.14
NMR: 200 MHz (CDCl₃) 0.9–1.0(t,3H),1.1–1.2(two doublets,6H),1.4–1.7(m,4H), 1.9–2.1(m,2H),4.5–4.9(ABq,2H),5.0–5.2(m,1H),7.0–7.4(m,6H),7.8(s,1H).

EX. No. 15
NMR: 200 MHz (CDCl₃) 0.9–1.0(t,3H),1.3–1.7(m,4H),1.9–2.1(t,2H),3.3(s,3H),3.5–3.6(t,2H), 4.24.4(t,2H),4.6–4.9(ABq,2H),7.1–7.4(m,4H),7.4(s,1H) and 7.8(s,1H).

EX. No. 43
NMR: 60 MHz (CDCl₃) 1.1–2.4(m,9H),1.4–1.6(d,6H)4.9–5.4(ABq,2H),5.3–5.5(t,1H), 7.0–7.2(d,1H),7.3–7.5(dd,1H),7.65–7.7(d,1H),7.6(s,1H) and 8.0(s,1H).

EX. No. 44
NMR: 60 MHz (CDCl₃) 0.7–2.1(m,16H),4.0–4.3(t,2H),4.7–5.2(ABq,2H),6.8–7.0(d,1H) 7.1–7.3(dd,1H),7.5–7.55(d,1H),7.4(s,1H) and 7,9(s,1H).

EX. No. 45
NMR: 60 MHz (CDCl₃) 0.8–1.0(d,6H),1.2–2.2(m,10H),3.9–4.1(d,2H),4.7–5.3(ABq,2H) 6.9–7.1(d,1H),7.1–7.5(dd,1H),7.5–7.6(d,1H),7.4(s,1H) and 8.0(s,1H).

EX. No. 47
NMR: 60 MHz (CDCl₃) 0.8–2.4(m,9H),5.0–5.4(ABq,2H),5.1–5.4(ABq,2H), 6.7–7.6(d,9H),8.0(s,1H) and 8.1(s,1H).

EX. No. 48
NMR: 60 MHz (CDCl₃) 1.0–2.2(m,9H),2.3(br s,1H),3.7–3.9(9br t,2H),4.2–4.4(br t,2H), 4.8–5.2(ABq,2H),7.0–7.6(m,3H),7.6(s,1H) and 7.9(s,1H).

EX. No. 49
NMR: 60 MHz (CDCl₃) 0.9–1.6(m,12H),2.3(br s,1H),3.8–3.9(d,1H), 4.3(m,2H),5.0–5.3(ABq,2H),7.0–7.5(m,3H),7.8(s,1H) and 7.9(s,1H).

EX. No.50
NMR: 60 MHz (CDCl₃) 0.9–2.1(m,9H),3.5(s,3H),4.9–5.0(br d 1H),5.2–5.5(ABq, 2H),6.9–7.0(d,1H),7.1–7.3(dd,1H),7.45–7.5(d,1H),7.4(s,1H) and 7.8(s,1H).

EX. No. 51
NMR: 60 MHz (CDCl₃) 0.8–1.6(m,9H),3.3(s,3H),3.4–3.7(t,2H),4.2–4.4(t,2H), 4.8–5.0(ABq,2H),6.8–7.5(m,3H),7.4(s,1H), and 7.8(s,1H).

EX. No. 52
NMR: 60 MHz (CDCl₃) 1.0–1.6(m,15H),3.6–4.0(m,2H),4.8–5.4(ABq,2H),6.1–6.3(t,1H), 7.0–7.2(d,1H),7.2–7.5(dd,1H),7.65–7.7(d,1H),7.4(s,1H) and 7.9(s,1H).

EX. No.53
NMR: 60 MHz (CDCl₃) 1.0–2.2(m,12H),5.0–5.1(br s,2H),5.5–5.8(m,1H),7.0–7.77(m,3H), 7.5(s,1H) and 8.0(s,1H).

EX. No. 54
NMR: 60 MHz (CDCl₃) 1.0–2.4(m,9H),3.9(s,3H),4.4–5.4(ABq,2H),7.2–7.6(m,3H),7.5(s,1H), and 8.0(s,1H).

EX. No. 55
NMR: 60 MHz (CDCl₃) 0.9–2.0(m,9H),1.3–1.5(two overlapping d,3H),3.8(s,3H),4.7–4.9(br s, 2H),5.1–5.3(q,1H),7.0–7.5(m,3H),7.5(s,1H) and 7.8(s,1H).

EX. No. 56
NMR: 60 MHz (CDCl₃) 1.0–1.9(m,9H),2.1s,3H),4.3–4.6(m,4H),5.0–5.2(ABq,2H), 6.9–7.2(d,1H),7.2–7.4(dd,1H),7.5–7.55(d,1H),7.4(s,1H) and 7.9(s,1H).

EX. No. 57
NMR: 60 MHz (CDCl₃) 1.0–2.1(m,9H),2.5(t,1H),4.8–5.0(q,2H),5.1–5.2(s,2H),7.0–7.6(m,3H), 7.5(s,1H) and 7.9(s,1H).

EX. No. 58
NMR: 60 MHz (CDCl₃) 0.9–2.1(m,9H),4.5–5.2(ABq,2H),4.9–5.0(d,2H),5.4(s,2H), 6.9–7.1(d,1H),7.2–7.4(dd,1H),7.4–7.5(d,1H),7.4(s,1H), and 7.8(s,1H).

EX. No. 59
NMR: 60 MHz (CDCl₃) 0.9–2.1(m,9H),3.9(s,3H),4.9(s,2H),5.4–5.8(br s,2H),6.9–7.1(m,3H), 7.2(s,1H),7.8(s,1H).

EX. No. 60
NMR: 200 MHz (d₆-DMSO): 0.9–2.0(m,9H),3.8(s,3H),4.8–5.0(ABq,2H),6.7–7.2(m,4H),7.4(br s,1H) and 7.8(br s,1H).

EX. No. 61
NMR: 60 MHz (CDCl₃) 0.9–1.0(t,3H),1.2–2.1(m,6H),3.7(s,3H),3.85(s,3H), 4.8(br s,2H),6.8–7.0(m,3H),7.1(s,1H),7.3–7.4(m,1H) 7.8(s,1H).

EX. No. 62
NMR: 200 Hz (CDCl₃) 0.9–1.0(t,3H),1.1–2.1(t,3H),1.1–2.1(m,6H),3.8(s,3H),4.1–4.3(ABq,2H), 4.8(s,2H) and 6.9–7.4(m,5H).

EX. No. 63
NMR: 200 MHz (CDCl₃)0.9–1.0(t,3H),1.2–2.1(m,6H),3.8(s,3H),4.4–4.7(m,2H),4.8(s,2H), 6.8–7.4(m,5H) and 7.8(s,1H).

EX. No. 64
NMR: 60 MHz (CDCl₃) 1.0–2.3(m,15H),3.9(s,3H),4.9(s,2H),5.0–5.3(t,1H), 6.9–7.5(m,5H), and 7.9(s,1H).

EX. No. 65
NMR: 60 MHz (CDCl₃) 0.9–2.1 (m,9H),3.4(s,3H),3.9(s,3H),4.9(s,2H),5.3(s,2H), 6.9–7.6(m,5H), and 7.9(br s,1H).

EX. No. 66
NMR: 60 MHz (CDCl₃) 0.9–2.1(m,9H),3.3(s,3H),3.6(m,2H),3.8(s,3H),4.2(m,2H),4.8(s,2H), 6.8–7.3(m,5H), and 7.8(br s,1H).

EX. No. 67
NMR: 60 MHz (CDCl₃) 0.9–2.1(m,12H),3.4–3.7(two overlapping ABq,4H),3.9(s,3H) 4.2–4.4(m,2H),4.9(s,2H),7.0–7.4(m,5H), and 8.0(s,1H).

EX. No. 68
NMR: 60 MHz (CDCl₃) 0.9–2.3(m,12H),4.0(two s,3H),4.9(s,2H),5.4–5.8(q,1H), 6.9–7.6(m,8H), and 8.0(s,1H).

EX. No. 69
NMR: 200 MHz (CDCl₃)0.9–1.1(t,3H),1.3–1.4(br s,9H),1.4–2.0(m,6H),3.8(s,3H), 0.7–4.8(ABq,2H),6.8–7.3(m,4H),7.0(s,1H), and 7.8(s,1H).

EX. No. 70
NMR: 200 MHz (CDCl₃) 0.9–1.0(t,3H),1.1–2.0(m,6H),2.45–2.55(m,1H),2.7–2.80(t,1H), 3.1–3.15(m,1H),3.8(s,3H),3.9–4.0(m,1H),4.8(br s,2H), 6.8–7.3(m,5H), and 7.7(s,1H).

EX. No. 72
NMR: 200 MHz (CDCl₃)0.9–1.1(t,3H),1.2–1.3(t,3H),1.4–1.5(t,3H),1.6–2.0(m,6H), 4.0–4.3(m,4H),4.8(br s,2H),6.8–7.2(m,4H),7.3 (s,1H), and 7.8(s,1H).

EX. No. 73
NMR: 200 MHz (CDCl₃)0.9–1.1(t,3H),1.4(s,9H),1.3–1.5(m,4H),1.7–1.9(m,2H)4.0–4.2(m,2H), 4.7–5.0(ABq,2H),6.7–7.3(m,4H),7.0(s,1H), and 7.8(s,1H).

EX. No. 74

NMR: 200 MHz (CDCl$_3$) 0.8–0.9(t,3H),0.-
9–1.0(t,3H),1.0–1.2(t,3H),1.2–2.0(m,8H),
3.9–4.2(m,4H),4.9(s,2H),6.8–7.3(m,5H) and
7.8(s,1H),1H).

EX. No. 75

NMR: 200 MHz (CDCl$_3$) 0.9–1.0(t,3H),1.-
0–1.1(t,3H),1.3(s,9H),1.5–2.0(m,8H),3.9–4.1(t,2H),
4.7–5.0(ABq,2H),6.7–7.2(m,4H),7.0(s,1H), and
7.8(s,1H).

EX. No. 76

NMR: 200 MHz (CDCl$_3$) 0.9–1.0(t,3H),1.-
0–1.15(t,3H),1.2–1.25(d,3H),1.3–1.36(d,3H),
1.40–1.42(d,3H),1.4–2.0(m,6H),4.6–4.8(m,1H), 4.8(br
s,2H),4.95–5.10(m,1H),6.7–7.0(m,4H),7.2–7.4(m,1H)
and 7.8(s,1H).

EX. No. 77

NMR: 200 MH$_z$(CDCl$_3$) 0.9–1.1
(q,3H),1.4(s,9H),1.3–2.0(m,13H), 4.0–4.1(t,2H),4.7–5.-
0(ABq,2H),6.7–6.9(m,3H),6.9(s,1H),7.2–7.3(m,1H) and
7.8(s,1H).

EX. No. 78

NMR: 200 MHz (CDCl$_3$) 0.9–1.1(t,3H),1.-
2–2.1(m,6H),2.4–2.45(t,1H),2.5–2.55t,1H), 4.6–5.0(-
three overlapping ABq,6H),6.8–7.1(m,3H),
7.1(s,1H),7.2–7.3(m,1H) and 7.7(s,1H).

EX. No. 79

NMR: 200 MHz (CDCl$_3$) 0.9–1.0(t,3H),1.-
2–2.1(m,6H),3.25(s,3H),3.45(s,3H),3.5–3.6(t,2H),3.-
7–3.8(t,2H),4.0–4.9(m,4H),4.7–5.0 (ABq,2H),6.-
7–6.9(m,3H),7.0(s,1H),7.71–7.2(m,1H), and 7.7(2,1H).

EX. No. 80

NMR: 200 HZ (d$_6$DMSO): 0.8–1.4(two overlapping
doublets,6H),1.0–1.6(m,3H), 1.7–2.1(m,2H),4.6–4.-
9(ABq,2H),7.0–7.3(m,4H),7.9(s,1H) and 7.95(s,1H).

EX. No. 81

NMR: 200 MHZ (CDCl$_3$) 0.8–1.2(m,11H),1.-
4–1.8(m,3H),1.9–2.1(m,2H),4.0–4.2(m,2H), 4.5–4.-
8(ABq,2H),7.0–7.2(m,4H),7.4(s,1H), and 7.8(s,1H).

EX. No. 82

NMR: 200 MHZ (CDCl$_3$)0.8–1.2(m,7H),1.-
4–1.7(m,2H),1.9–2.1(m,2H),3.3(s,3H), 3.5–3.6(m,2H),4.-
2–4.5(m,2H),4.6–4.9(ABq,2H),6.9–7.2 (m,4H),7.5(s,1H)
and 7.8(s,1H).

EX. No. 83

NMR: 200 MHZ (CDCl$_3$) 1.3–2.0(m,8H),2.-
4–2.6(m,1H),4.6–4.9(ABq,2H),6.9(m,4H),7.7(s,1H) and
7.8(s,1H).

EX. No. 84

NMR: 200 MHZ (d$_6$-DMSO) 1.6–2.2(m,8H),2.-
6–2.8(m,1H),3.8(s,3H),4.6–5.0(ABq,2H),
6.7–7.3(m,5H), and 7.8(s,1H).

EX. No. 85

NMR: 200 MHZ (d$_6$-DMSO) 1.2–2.2(m,8H),2.-
6–2.7(m,1H),3.8(s,3H),4.6–5.0(ABq,2H),
6.8–7.2(m,4H),7.4(s,1H) and 7.7(s,1H).

EX. No. 86

NMR: MHZ (CDCl$_3$)
1.4–2.8(m,9H),3.7(s,3H),3.9(s,3H),4.7(s,2H),6.-
8–7.3(m,5H), and 7.8(s,1H).

EX. No. 87

NMR: 200 MHZ (CDCl$_3$) 1.1–1.9(m,10H),2.-
0–2.1(m,1H),4.7–4.9(ABq,2H),7.0–7.3(m,4H), 7.7(s,1H)
and 7.9(s,1H).

EX. No. 88

NMR: 200 MHZ (CDCl$_3$)
1.1–2.2(m,11H),3.7(s,3H),3.8(s,3H),4.6–5.1(ABq,2H),6.-
8–7.3(m,5H) and 7.8(s,1H).

EX. No. 89

NMR: 200 MHz (CDCl$_3$) 3.2–3.8(ABq,2H),4.6–5.-
0(ABq,2H),6.9–7.5(m,8H),7.8(s,1H), and 7.9(s,1H).

EX. No. 90

NMR: 200 MHz (CDCl$_3$) 0.9–1.4(two
d,6H),3.8–4.2(d,2H),4.8–5.2(ABq,2H),7.0–7.7(m,9H),
and 8.0(br s,1H).

EX. No. 91

NMR: 200 MHz (CDCl$_3$) 3.3(s,3H),3.2–3.6(m,4H),4-
.1–4.4(m,2H), 4.7–5.2(ABq,2H),7.0–7.7(m,9H), and
8.0(br s,1H).

EX. No. 92

NMR: 200 MHz (d$_6$-acetone) 3.3–3.8(ABq,2H),4-
.4–4.9(ABq,2H),6.9–7.6(m,9H),7.7(s,1H), and 7.9(s,1H).

EX. No. 93

NMR: 200 MHz (CDCl$_3$) 1.1–1.2(t,3H) 3.3–3.-
8(ABq,2H),4.1–4.2(q,2H),4.64–4.8(ABq 2H),
6.9–7.5(m,10H), and 7.9(s,1H).

EX. No. 94

NMR: 200 MHz (CDCl$_3$) 3.2–3.4(ABq,2H),4.6–4.-
9(ABq,2H),6.8–7.3(m,9H),7.7(s,1H), and 7.8(s,1H).

EX. No. 95

NMR: 200 MHz (d$_6$-DMSO) 2.9–3.5(ABq,2H),3.5(br
s,3H),4.2–4.6(ABq,2H),6.5–7.3(m,11H), 7.8(br s,1H).

EX. No. 96

NMR: 200 MHz (CDCl$_3$) 3.1–3.5(ABq,2H),3-
.8–3.9(br s,3H),4.3–4.9(ABq,2H),6.7–7.4(m,9H),
7.8(s,1H), and 7.9(s,1H).

EX. No. 97

NMR: 200 MHz (CDCl$_3$) 3.2–3.-
8(ABq,2H),3.6(s,3H),3.8(s,3H),4.7(s,2H),6-
.9–7.5(m,10H), and 7.9(s,1H).

EX. No. 98

NMR: 200 MHz (CDCl$_3$) 1.0–1.2(t,3H),3.2–3.-
7(ABq,2H),3.8(s,3H),4.0–4.1(q,2H),4.7–4.8(br
s,2H),6.8–7.6(m,10H) and 7.8(s,1H).

EX. No. 99

NMR: 200 MHz (CDCl$_3$) 3.2–3.-
8(ABq,2H),3.8(s,3H),4.2–4.5(m,2H),4.85(s,2H),
6.8–7.6(m,10H), and 7.9(s,1H).

EX. No. 100

NMR: 200 MHz (CDCl$_3$)0.7–0.8(t,3H),1-
.4–1.6(m,2H),3.1–3.7(ABq,2H),3.8(s,3H),
3.9–4.0(t,2H),4.7–4.8(ABq,2H),6.8–7.6(m,10H), and
7.9(s,1H).

EX. No. 101

NMR: 200 MHz (CDCl$_3$) 3.3(s,3H),3.3–3.6(m,2H),3-
.2–3.7(ABq,2H),3.8(s,3H),4.0–4.3(m,2H), 4.7–4.-
9(ABq,2H),6.8–7.6(m,10H), and 7.9(s,1H).

EX. No. 102

NMR: 200 MHz (d$_6$-DMSO) 2.5(br s,1H),3.3–3.-
6(ABq,2H),3.7(s,3H),4.4–4.8(ABq,2H), 6.8–7.2(q,4H),7-
.2–7.5(m,5H),7.8(s,1H), and 8.0(s,1H).

EX. No. 103

NMR: 200 MHz (CDCl$_3$)0.8–0.9(t,1H),1-
.5–1.8(m,2H),3.3.–3.6(ABq,2H),3.8(s,1H),
3.9–4.2(m,2H),4.5–4.8(ABq,2H),6.8–7.0(q,4H),7-
.2–7.5(m,6H) and 7.9(s,1H).

EX. No. 104

NMR: 200 MHz (CDCl$_3$) 3.3(s,3H),3.4–3.-
6(ABq,2H),3.5–3.6(m,2H),3.8(s,3H),3.8(s,3H),
4.2–4.4(m,2H),4.5–4.8(ABq,2H),6.8–7.0(q,4H),
7.3–7.5(m,6H), and 7.9(s,1H).

EX. No. 105

NMR: 200 MHz (CDCl$_3$) 1.3–1.4(t,3H),3.0–3.-
2(ABq,2H),3.5(s,3H),3.9–4.2 (m,2H),4.7–4.-
8(ABq,2H),6.7–7.5(m,10H), and 7.8(s,1H).

EX. No. 106

NMR: 200 MHz (CDCl₃) 1.0–1.15(t,3H), 1.4–1.5(t,3H),3.2–3.7(ABq,2H),3.9–4.2(m,4H), 4.7–4.9(ABq,2H),6.8–7.5(m,10H), and 7.8(s,1H).
EX. No. 107
NMR: 200 MHz (CDCl₃) 0.7–0.8(t,3H),1.3–1.5(t,3H),1.4–1.6(m,2H),3.2–3.7(ABq,2H), 3.8–4.2(m,4H),4.7–4.9(ABq,2H),6.8–7.5((m,9H), 7.5(s,1H) and 7.9(s,1H).
EX. No. 108
NMR: 200 MHz (CDCl₃) 0.9–1.0(d,3H),1.2–1.3(d,3H),1.8–2.0(t,3H),3.2–3.7(ABq,2H), 4.0–4.2(m,4H),4.7–5.0(m,3H),6.8–7.5(m,9H),7.5(s,1H), and 7.8(s,1H).
EX. No. 109
NMR: 200 MHz (CDCl₃) 1.3–1.4(t,3H),3.3(s,3H),3.2–3.7(ABq,2H),3.3–3.5(m,2H), 3.9–4.2(m,2H),4.7–4.9(ABq,2H),6.7–7.5(m,9H),7.5(br s, 1H) and 7.8(s,1H).
EX. No. 110
NMR: 200 MHz (CDCl₃) 0.8–0.9(t,3H),1.1–1.4(m,4H),1.3–1.5(t,3H),3.1–3.5 (m,2H),3.9–4.0(t,3H),3.9–4.2(m,2H),4.7–4.9(ABq,2H),6.8–7.5(m,10H), and 7.8(s,1H).
EX. No. 111
NMR: 200 MHz (CDCl₃) 0.7–0.8(two overlapping doublets,6H),1.3–1.4(t,3H), 1.6–1.7(m,1H),3.2–3.6(ABq,2H),3.6–3.7(d,2H),3.9–4.2 (m,2H),4.7–4.9(ABq,2H),6.8–7.5(m,10H), and 7.9(s,1H).
EX. No. 112
NMR: 200 MHz (CDCl₃) 1.0–1.1(t,3H),1.4–1.5(br s,9H),1.5–1.6(m,4H),1.8–1.9 (m,3H), 4.0–4.2(m,2H),4.7–5.0(ABq,2H),6.8–7.3(m,5H), and 7.8(s,1H).
EX. No. 113
NMR: 200 MHz (CDCl₃)0.7–0.8(t,3H),1.0–1.1(t,3H),1.4–1.6(m,2H),1.7–1.9 (m,2H),3.2–3.8(ABq,2H),3.8–4.0(m,4H),4.8(br s,2H),6.8–7.5(m,10H), and 7.8(s,1H).
EX. No. 114
NMR: 200 MHz (CDCl₃) 0.8(br s,3H),1.2(br s,3H),1.3–1.5(d,6H),3.2–3.6(ABq,2H), 4.6–5.0(m,4H),6.8–7.5(m,(H),7.5(br s,1H), and 7.7(br s,1H).
EX. No. 115
NMR: 200 MHz (CDCl₃) 0.8–1.8(m,14H),3.2–3.7(ABq,2H),3.9–4.1(m,4H), 4.7–4.8(br s,2H),6.8–7.5(m,9H),7.6(br s,1H), and 7.9 (br s,1H).
EX. No. 116
NMR: 200 MHz (CDCl₃) 3.2–3.8(ABq,2H),4.4–4.5(d,2H),4.5–4.6(dd,2H),4.7–4.9(ABq,2H), 5.0–5.4(m,4H),5.6–5.8(m,1H),5.9–6.2(m,1H), 6.8–7.5(m,10H), and 7.9(S,1H).
EX. No. 117
NMR: 200 MHz (CDCl₃) 3.2(s,3H),3.3–3.6(m,5H),3.7–3.8(m,3H),4.7–5.0(ABq,2H), 6.8–7.5(m,9H),7.5(br s,1H), and 7.8(br s,1H).
EX. No. 118
NMR: 200 MHz (CDCl₃) 3.4–3.7(ABq,2H),4.7–5.0(ABq,2H),6.8–7.3(m,8H),7.7(s,1H), and 7.8A(s,1H).
EX. No. 119
NMR: 200 MHz (CDCl₃) 3.6(s,3H),3.75(s,3H),4.7–4.9(ABq,2H),6.8–7.4 (m,8H),7.8(s,1H), and 7.9–8.0(dd,1H).
EX. No. 120
NMR: 200 MHz (CDCl₃) 1.0–1.1(t,3H),3.7(s,3H),3.6–3.8(ABq,2H),3.9–4.2 (m,4H),4.7–4.9(ABq,2H),6.8–7.4(m,8H),7.8(s,1H) and 7.9–8.0(dd,1H).
EX. No. 121
NMR: 200 MHz (CDCl₃) 1.0–1.1(t,3H),1.2–1.4(d,2H),3.6–3.9(m,3H),3.7H), 4.7–5.0(ABq,2H),6.8–7.5(m,8H),7.8(s,1H),7.9–8.0 (dd,1H).

EX. No. 122
NMR: 200 MHz (CDCl₃) 1.0–1.1(t,3H),1.4(t,3H),3.6–3.9(ABq,2H),3.9–4.2 (m,4H),4.7–5.0(ABq,2H),6.8–7.4(m,9H),7.8(s,1H), and 7.9–8.0(dd,1H).
EX. No. 123
NMR: 200 MHz (CDCl₃) 3.1–3.3(t,1H),3.7–3.8(m,1H),3.9(s,3H),4.5–4.9(ABq,2H),5.5–6.2(br d,1H),6.8–7.6(m,8H),7.8(s,1H), and 7.9(S,1H).
EX. No. 124
NMR: 200 MHz (CDCl₃) 1.1–1.5(m,3H),3.2–3.8(m,8H),4.5–4.9(ABq,2H), 6.9–7.6(m,8H)7.8(s,1H) and 8.0(s,1H).
EX. No. 125
NMR: 200 MHz (CDCl₃) 1.1–1.4(m,6H),3.1–3.7(ABq,2H),3.9(s,3H), 4.5–4.9(ABq,2H),6.8–7.5(m,8H),7.8(s,1H), and 7.9(s,1H).
EX. No. 145
NMR: 200 MHz (CDCl₃) 2.1–2.6(m,4H),4.5–4.8(ABq,2H),6.9–7.4(m,8H),7.8(s,1H), and 7.9(s,1H).
EX. No. 146
NMR: 200 MHz (CDCl₃) 2.1–2.3(m,2H),2.5–2.7(m,1H),3.0–3.1(m,1H),3.8(s,3H), 4.8–5.0(ABq,2H),6.8–7.3(m,9H), and 7.9(1H).
EX. No. 147
NMR: 200 MHz (CDCl₃) 2.1–2.3(two overlapping ddd,2H),2.4–2.6(ddd,1H),2.9–3.1 (ddd,1H),3.7(s,3H),3.9(s,3H),4.7–5.0(ABq,2H),6.8–7.3(m,9H), and 7.8(s,1H).
EX. No. 148
NMR: 200 MHz (CDCl₃) 0.8–1.0(t,3H),1.5–1.8(m,2H),2.1–2.3(m,2H),2.4–2.6(m,1H), 2.9–3.2(m,1H),3.9(s,3H),4.0–4.2(m,2H), 4.8.0–5.0(ABq,2H),6.8–7.0(m,4H),7.2–7.4(m,5H), and 7.8(s,1H).
EX. No. 149
NMR: 200 MHz (CDCl₃) 2.1–2.2(m,2H),2.4–2.6(m,1H),2.9–3.1(m,1H),3.3(s,3H), 3.5–3.6(t,2H),3.9(s,3H),4.1–4.3(m,1H),4.4–4.6(m,1H), 4.8–5.0(ABq,2H),6.8–7.4(m,9H) and 7.8(s,1H).
EX. No. 150
NMR: 200 MHz (d₆-DMSO): 1.9–2.3(m,2H),2.4–2.8(m,2H),4.8–5.1(m,ABq,2H), 7.0–7.5(m,8H),8.0(s,1H), and 8.1(s,1H).
EX. No. 151
NMR: 200 MHz (CDCl₃) 0.8–0.9(t,3H),1.6–1.8(m,2H),2.1–2.3(m,2H),2.4–2.6(m,1H), 2.8–3.0(m,1H),4.1–4.3(m,2H),6.9–7.3(m,8H),7.5(s,1H), and 7.9(s,1H).
EX. No. 152
NMR: 200 MHz (CDCl₃) 2.1–2.3(m,2H),2.5–2.9(m,2H),3.3(s,3H), 3.6–3.65(t,2H),4.2–4.5(m,2H),4.6–5.0(ABq,2H),6.9–7.3(m,8H),7.5(s,1H), and 7.9(s,1H).
EX. No. 156
NMR: 200 MHz (CDCl₃) 0.3–2.3(m,19H),3.1–3.4(m,2H),4.5–5.0(m,4H),6.9–7.4(m,4H), and 7.8(s,1H).
EX. No. 163
NMR: 60 MHz (CDCl₃) 0.7–1.7(m,15H),4.5–4.7(m,2H),5.0–5.1(br d,1H),7.0–7.6(m,3H), 7.8(s,1H), and 8.0(s,1H).
EX. No. 164
NMR: 60 MHz (CDCl₃) 0.9–1.2(d,6H),1.1–2.2(m,12H),3.0–3.4(q,2H),4.8–5.2(ABq,2H) 5.2–5.5(t,1H),7.2–7.7(m,3H),7.5(s,1H) and 7.9(s,1H).
EX. No. 165
NMR: 60 MHz (CDCl₃) 0.9–1.2(m,9H),2.7–2.9(m,4H),3.6–4.1(m,4H),5.0–5.2(ABq,2H) 6.3–6.4(br s,1H),7.1–7.5(m,3H),7.4(s,1H) and 7.8(s,1H).
EX. No. 166

NMR: 60 MHz (CDCl₃) 0.9–1.9(m,9H),4.0(s,3H) 4.9(s,2H),5.4–5.8(br s,2H),6.9–7.1(m,3H), 7.2(s,1H), and 7.8(s,1H).

EX. No. 167

NMR: 60 MHz (CDCl₃) 3.2–4.1(ABq,2H) 4.6–5.3(ABq,2H),6.9–7.6(m,3H),7.8(s,1H) and 8.0(s,1H).

EX. No. 168

NMR: 200 MHz (d₆-DMSO) 3.4–3.7(ABq,2H),4.6–4.8(ABq,2H),6.9–7.6(m,11H),7.8(s,1H), and 8.0(s,1H).

EX. No. 169

NMR: 200 MHz (d₆-DMSO) 3.3–3.7(ABq,2H),4.3(s,3H),4.5–4.9(ABq,2H), 6.8–7.6(m,9H),7.7(s,1H), and 8.0(s,1H).

EX. No. 179A (higher Rf)N-R-(2-butanol)-2R isomer

NMR: 400 MHz (CDCl₃) 0.8(t,3H),1.3–1.5(m,2H),1.90–2.0(m,1H), 2.1–2.2(m,1H),2.6–2.7(m,1H),2.9–3.0(m,1H,3.5–3.7(ABq,2H),3.9–4. (m,1H),4.6–5.0(ABq,2H),5.5–5.6(d,1H),7.0–7.4(m,9H),7.3(s,1H), and 7.8(s,1H).

EX. No. 179B (lower Rf) N-R-(2-butanol)-2S isomer

NMR: 400 MHz (CDCl₃) 0.9(t,3H),1.4–6(m,2H),2.0–2.1(m,1H), 2.3–2.4(m,1H),2.55–2.65(m,1H),2.9–3(m,1H),3.5–3.7(ABq,2H), 3.9–4.(m,1H),4.65–5.05(ABq,2H),5.5–5.6(d,1H),7.1–7.4(m,9H), 7.3(s,1H) and 7.85(s,1H).

The 1,2,4-triazoles, and the enantiomorphs, acid addition salts and metal salt complexes thereof are useful as agricultural fungicides and, as such, can be applied to various loci such as the seed, the soil or the foliage. When used as herbicides, the compounds may be applied either to the plant itself or to the locus where control of undesired vegetation is needed. For such purposes these compounds can be used in the technical or pure form as prepared, as solutions or as formulations. The compounds are usually taken up in a carrier or are formulated so as to render them suitable for subsequent dissemination. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in the John W. McCutcheon, Inc. publication "Detergents and Emulsifiers, Annual."

In general, the compounds of this invention can be dissolved in certain solvents such as acetone, methanol, ethanol, dimethylformamide, pyridine or dimethyl sulfoxide and such solutions can be diluted with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent to enhance dispersion of the compound in water. The concentration of the active ingredient in emulsifiable concentrates is usually from about 10% to about 90%, and in flowable emulsion concentrates, can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 98%, preferably from about 40% to about 75%. A typical wettable powder is made by blending 50 parts of a 1,2,4-triazole, 45 parts of a synthetic precipitated hydrated silicon dioxide, such as that sold under the trademark Hi-Sil ®, and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silicoaluminate sold under the trademark Zeolex ®7.

Dusts are prepared by mixing the 1,2,4- triazoles, or the enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The 1,2,4-triazoles, and the enantiomorphs, salts and complexes thereof can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application, plants to be treated and diseases to be controlled. Generally, the compounds of this invention will be applied in amount of from about 0.05 pound to about 5.0 pounds per acre of the active ingredient.

As a seed protectant, the amount of toxicant coated on the seed is usually at a dosage rate of from about 0.05 to about 20, preferably from about 0.05 to about 4, and more preferably from about 0.1 to about 1 ounce per hundred pounds of seed. As a soil fungicide the chemical can be incorporated in the soil or applied to the surface usually at a rate of from about 0.02 to about 20, preferably from about 0.05 to about 10, and more preferably from about 0.1 to about 5 pounds per acre. As a foliar fungicide, the toxicant is usually applied to growing plants at a rate of from about 0.01 to about 10, preferably from about 0.02 to 5, and more preferably from about 0.25 to about 1 pound per acre. pounds per acre.

Fungicides which can be combined with the fungicides of this invention include:

(a) dithiocarbamate and derivatives such as: ferbam, ziram, maneb, mancozeb, zineb, propineb, metham, thiram, the complex of zineb and polyethylene thiuram disulfide, dazomet, and mixtures of these with copper salts;

(b) nitrophenol derivatives such as: dinocap, binapacryl, and 2-sec-butyl-4,6-dinitrophenyl isopropyl carbonate;

(c) heterocyclic structures such as: captan, folpet, glyodine, anilazine, ditalimfos, 4-butyl-1,2,4-triazole, 5-amino- 1-[bis(dimethylamino)phosphinyl]-3-phenyl-1,2,4-triazole, etradiazole, dithianon, thioquinox, benomyl, thiabendazole, 4-(2-chlorophenyl-hycirazono)-3-methyl-5-isoxazolone, vinclozolin, iprodione, procymidone, triadimenol, triadimefon, bitertanol, prochloraz, fenarimol, bis-(p-chlorophenyl)-3-pyridinemethanol, bis-(p-chlorophenyl)-5- pyrimidinemethanol, triarimol, flutriafol, flusilazole, propiconazole, ectaconazole, myclobutanil, alpha-[2-(4-chlorophenyl)ethyl]-alpha-phenyl-1H-1,2,4-triazole-1-propanenitrile, hexaconazole, cyproconazole, tebuconazole, diniconazole, fluoroimide, pyridine-2-thiol-1-oxide, 8-hydroxyquinoline sulfate and metal salts thereof, 2,3-dihydro-5-carboxanilido-6-methyl-1,4-oxathiin-4,4-dioxide, 2,3-dihydro-5-carboxanilido-6-methyl-1,4-oxathiin, cis-N-[(1,1,2,2-tetrachloroethyl)thiol]-4-cyclohexene-1,2-dicarboximide, cycloheximide, dehydroacetic acid, captafol, ethirimol, quinomethionate, D,L-methyl-N-(2,6-dimethylphenyl)-N-(2'-methoxyacetyl)alanine methyl ester, D,L-methyl-N-(2,6-dimethylphenyl)-N-chloroacetyl-D,L-2-aminobutyrolactone, D,L-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-(methoxymethyl)-1,3-oxazolidi-2,4-dione, 3-(3,5-dichlorophenyl)-1-isopropylcarbamoylhydantoin, 2-cyano-[N-(ethylaminocarbonyl)-2-methoximino]acetamide, fenpropimorph, fenpropidine, 2,6-dimethyl-N-tridecylmorpholine, dodemorph, and triforine;

(d) miscellaneous halogenated fungicides such as: chloranil, dichlone, chloroneb, tricamba, TCPN, dichloran, 2-chloro-1-nitropropane, polychloronitrobenzenes such as pentachloronitrobenzene (PCNB), and tetrafluorodichloroacetone;

(e) fungicidal antibiotics such as: griseofulvin, kasugamycin, polyoxin, validamycin, and streptomycin;

(f) copper-based fungicides such as: copper hydroxide, cuprous oxide, basic cupric chloride, basic copper carbonate, copper terephthalate, copper naphthenate and Bordeaux mixture; and (g) miscellaneous fungicides such as: dodine, phenylmercuric acetate, N-ethylmercuri-1,2,3,6-tetrahydro-3,6-endomethano-3,4,5,6,7,7-hexachlorophthalimide, phenylmercuric monoethanol ammonium lactate, p-dimethylaminobenzene sodium sulfonate, methyl isothiocyanate, 1-thiocyano-2,4-dintrobenzene, 1-phenylthiosemicarbazide, nickel-containing compounds, calcium cyanamide, lime sulfur, thiophanate-methyl, flutolanil, edinophos, isoprothiolane, propenazole, and tricyciazole.

The 1,2,4-triazoles, and the enantiomorphs, acid addition salts and metal salt complexes thereof can be advantageously employed in various ways. Since these compounds possess broad spectrum fungicidal activity, they can be employed in the storage of cereal grain. These complexes can also be employed as fungicides in cereals including wheat, barley and rye, in rice, peanuts, beans and grapes, on turf, in fruit, nut and vegetable orchards, and for golf course applications.

Examples of diseases against which the compounds of the invention are useful include helminthosporium of corn and barley, wheat and barley powdery mildew, wheat leaf and stem rusts, tomato early blight, tomato late blight, peanut early leaf spot, grape powdery mildew, grape black rot, apple scab, apple powdery mildew, cucumber powdery mildew, brown rot of fruits, botrytis, bean powdery mildew, cucumber anthracnose, wheat septoria nodorum, rice sheath blight and rice blast.

The herbicidal compounds of this invention are applied to the plant or plant habitat in any amount which will be sufficient to effect the desired plant response without causing a significant undesirable phytotoxic response. Generally, the compounds will be applied to the plant or plant habitat at a rate (treating level) of about 0.1 to 10, preferably about 0.4 to 20, and most preferably about 2 to 5 pounds per acre.

The herbicidal compounds can be used either individually or in mixtures. Under some conditions, the compounds may be used advantageously with other agricultural chemicals such as fertilizers, herbicides, fungicides, insecticides, and plant bactericides. For example, they can be used in combination with other herbicides and plant growth regulators, such as auxins, gibberellins, ethylene-releasing agents such as ethephon, pyridones, cytokinins, maleic hydrazide, succinic acid 2,2-dimethylhydrazide, choline and its salts, (2-chloroethyl)trimethylammonium chloride, triiodobenzoic acid, tributyl-2,4-dichlorobenzylphosphonium chloride, polymeric N-vinyl-2-oxazolidinones, tri(dimethylaminoethyl) phosphate and its salts, and N-di-methylamino-1,2,3,6-tetrahydrophthalamic acid and its salts.

Other herbicidal compounds with which the compounds may be used include
2-chloro-2',6'diethyl-N-(methoxymethyl)acetanilide,
2-chloro-2',6'diethyl-N-(butoxymethyl)acetanilide,
S-[4-chlorophenyl)-methyl]-diethylcarbamothioate,
2-t-butyl-4-(2,4-dichloro-5-isopropoxyphenyl-2-1,3,4-oxadiazolin-5-one,
2,4-dichloro-1-(3'-methoxy-4'-nitrophenoxy)benzene, (2,4-dichlorophenoxy)acetic acid,
2-methyl-4-chlorophenoxyacetic acid, 2-(2,4,5-trichlorophenoxy)propionic acid,
7-oxabicyclo[2,2.1]heptane-2,3-dicarboxylic acid; S-ethyl hexahydro-1H-azepine-1-carbothioate, 3',4-dichloropropionanilide, and
2,4-dichlorophenyl p-nitrophenyl ether.

The following Examples are provided to further illustrate the methods of preparation of the compounds of the present invention.

EXAMPLE 16 (Procedure A)

2-(4-chlorophenyl)-2-[(1,2,4-triazol-1-yl)methyl]hexanoic acid

To a 500 milliliter (mL) flask was charged 60.0 grams (g) (0.208 mole) of alpha-n-butyl-alpha-(4-chlorophenyl)-1H-1,2,4-triazole-1-propanenitrile followed by 200 mL of 48% hydrobromic acid. The mixture was stirred at reflux for 96 hours after which gas-liquid chromatography (GLC) indicated disappearance of the starting material. The reaction was diluted with ethyl ether and extracted with water until pH neutral. The ether was extracted with sufficient 10% sodium hydroxide to pH 14 followed by separation with 35% hydrochloric acid at which time a white solid precipitate formed. The solid was collected by filtration and washed with water until the aqueous rinse was neutral. The product was dried under vacuum and gave 49.0 g (76.5% yield) of a white solid, Example 1b of Table 1.

EXAMPLE 162 (Procedure B)

2-(2,4-dichlorophenyl)-2-[(1,2,4-triazol-1-yl)methyl]-hexanoamide

To a 250 mL flask was charged 38.16 g (0.119 mole) of alpha-n-butyl-alpha-(2,4-dichlorophenyl)-1H-1,2,4-triazole-1-propane-nitrile followed by 100 mL (0.63 mole) of 48% hydrobromic acid. The mixture was stirred at reflux for 48 hours after which GLC indicated disappearance of the starting material. The reaction was cooled to room temperature and neutralized with concentrated ammonium hydroxide (100 mL) to pH 8 and then to neutral pH with concentrated hydrochloric acid. A gummy oil formed which was taken up with 200 mL of ethyl acetate. The aqueous was extracted twice more with 200 ml portions of ethyl acetate and the combined ethyl acetate portions were then washed three times with 100 mL portions of water. The organic phase was dried and concentrated to give a tan solid which was recrystallized from ethyl ether. The product was filtered and gave 22.78 g (56.3% yield) of a solid, Example 162 of Table 1.

EXAMPLE 157 (Procedure B)

2-(4-chlorophenyl)-2-[(1,2,4-triazol-1-yl)methyl]hexanoamide

To a 500 mL flask was charged 75.0 g (0.24 mole) of alpha-n-butyl-alpha-(4-chlorophenyl)-1H-1,2,4-triazole-1-propanenitrile followed by 300 mL of 95% sulfuric acid. The mixture was stirred at 90° C. for 7 days after which the mixture was cooled to room temperature, diluted with ice and neutralized with ammonium hydroxide until basic (pH 8). The product was extracted with ethylene dichloride then washed with water and dried over magnesium sulfate. The solvent was concentrated and gave 45 g (56.5% yield) of a solid, Example 157 of Table 1.

EXAMPLE 153 (Procedure B)

2-(4-chlorophenyl)-2-[(1,2,4-triazol-1-yl)methyl]butyramide

To a 500 mL flask was charged 100.0 g (0.38 mole) of alpha-(4-chlorophenyl)-alpha-ethyl-1H-1,2,4-triazole-1-propanenitrile and 100 mL of dimethyl sulfoxide. To the stirring solution was added 100 g (1.25mole) of 50% sodium hydroxide. The reaction mixture was heated at 100° C. for 1 hour after which GLC indicated the starting material was consumed. The reaction was poured into water and extracted with ethyl acetate. After washing with brine, the organic phase was dried over magnesium sulfate and concentrated under vacuum without heating. Removal of the solvent gave a foamy glassy solid which was triturated with hexane, filtered and gave 97 g (91% yield) of a white solid, Example 153 of Table 1.

EXAMPLE 154 (Procedure B)

2-(2,4-dichlorophenyl)-2-[(1,2,4-triazol-1-yl)methyl]butyramide

To a 1 liter flask was charged 206.5 g (0.7 mole) of alpha-(2,4-dichlorophenyl)-alpha-ethyl-1H-1,2,4-triazole-1-propanenitrile and 500 mL of dimethylsulfoxide and 200 mL of water. To the stirring solution was added 67.2 g (0.84 mole) of 50% sodium hydroxide. The reaction mixture was heated at 91° C. (steam bath) for 3 hours after which GLC indicated the starting material was consumed. The reaction was cooled to 30° C. then poured into water and extracted with ethyl acetate. After drying, the ethyl acetate was treated with charcoal and filtered through Celite®. Removal of the solvent gave a foamy oil which was stirred and diluted with ethyl acetate then triturated with hexane until cloudy. This mixture was cooled at 0° C. for about 1 hour after which a solid formed. The product was filtered and washed with ether and hexane then dried and provided 172 g (79% yield) of a white solid, Example 154 of Table 1.

EXAMPLE 170 (Procedure B)

4-(4-chlorophenyl)-2-phenyl-2-[(1,2,4-triazol-1-yl)-methyl]butyramide

To a 2 L flask was charged 320.0 g (0.95 mole) of alpha-(2-(4-chlorophenyl)ethyl)-alpha-phenyl-1H-1,2,4-triazole-1-propanenitrile, 685 mL dimethylsulfoxide and 275 mL of water. To the stirred solution was added 91.3 g(1.14 moles) of 50% sodium hydroxide. The reaction mixture was heated at 95° C. for 3 hours after which GLC indicated the starting material was consumed. The reaction was cooled to 20° C. and the mixture was transferred to a 5 liter separatory funnel to which was added 1000 mL ethyl acetate and 3000 mL of water. A solid separated and the aqueous phase was removed. An additional 1000 mL of ethyl acetate was added and the mixture heated to 55° C. to dissolve the solids. Additional aqueous phase separated and was extracted with 500 mL of ethyl acetate. The organic phases were combined and washed with 1 liter of warm water and 50 0 mL of saturated sodium chloride solution (brine). Drying over magnesium sulfate and removal of the solvent gave 372 grams of a solid containing 10% ethyl acetate. Removal of the residual solvent gave a solid, Example 170 of Table 1.

EXAMPLE 1 (Procedure C)

2-(4-chlorophenyl)-2-[(1,2,4-triazol-1-yl)methyl]-butanoic acid

To a 500 mL flask was charged 95 g (0.34 mole) of 2-(4-chlorophenyl)-2-[(1,2,4-triazol-1-yl)methyl]butyramide and 95 g (0.97 mole) of 95% sulfuric acid and 95 g of ice. The reaction was stirred at reflux for 55 hours, after which the reaction was cooled to 10° C. and partitioned between ethyl acetate and water. The mixture was treated with 200 g of 10% sodium hydroxide which resulted in a pH 10 aqueous phase. The organic phase was extracted with 200 ml of water, then 200 ml of 10% sodium hydroxide and again with 200 mL of water. The aqueous phases were combined and washed with ethyl ether then acidified to pH 5 at which point a solid formed. The solid was filtered, washed with water, dried and gave 73 g (77% yield) of a white solid, Example 1 of Table 1.

EXAMPLE 5 (Procedure C)

2-(2,4-dichlorophenyl)-2-[(1,2,4-triazol-1-yl)methyl]-butanoic acid

To a 1 liter flask was charged 170 g (0.54 mole) of 2-(2,4-dichlorophenyl)-2-[(1,2,4-triazol-1-yl)methyl]-butyramide and 170 g (1.73 mole) of 95% sulfuric acid and 170 g of ice. The reaction was stirred at 113° C. (reflux) for 14 days after which the reaction was cooled to 10° C. and partitioned between ethyl acetate and water. The mixture was treated with 915 mL of 14% sodium hydroxide which resulted in a pH 10 aqueous phase. The mixture was stirred for 10 minutes and the aqueous layer was removed and extracted with additional ethyl acetate. The ethyl acetate was combined, washed with water, dried and concentrated to provide a solid; trituration with hexane yielded 95 g (55.8%) of starting amide.

The aqueous phase was acidified to pH 2 and 1000 mL of ethyl acetate was added and warmed to 50° C. An insoluble solid formed which was filtered, providing 28.5 g of acid. The phases were separated and the organic phase was washed with brine, dried and concentrated giving additional solid which was triturated with hexane and filtered providing 36.2 g of acid. The total product yield was 38%, melting point, Example 5 of Table 1

EXAMPLE 126 (Procedure C)

4-(4-chlorophenyl)-2-phenyl-2-[(1,2,4-triazol-1-yl)methyl]butanoic acid

To a 2 liter 3 neck flask was charged 220 g (0.62 mole) of 2-(4-chlorophenyl)-2-phenyl-2-[(1,2,4-triazol-1-yl)methyl]butyramide and 1000 mL (6.3 mole) of 48% hydrobromic acid. The reaction was heated at 80°-85° C. for 6 days then cooled to room temperature and poured into 4 liters of ice water. The solution was extracted with 2×1000 mL of water and brine. Drying over magnesium sulfate was followed by treatment with charcoal, then filtering through Celite ® and concentrating. The solid residue was slurried in ether, filtered and dried to give 139 g (63% yield), Example 126 of Table 1.

EXAMPLE 18 (Procedure D)

Ethyl 2-(4-chlorophenyl)-2-[(1,2,4-triazol-1-yl )methyl]-hexanoate

To a 250 mL 3 neck flask stirring under $N^2$ was charged 1.0 g of 60% sodium hydroxide (prewashed with hexanes) in 50 mL of dimethyl formamide (DMF). To the slurry was charged 6.14 g (0.020 mole) of 2-(4-chlorophenyl)-2-[(1,2,4-triazol-1yl)methyl]hexanoic acid in 50 mL of dimethyl formamide. The mixture was stirred at room temperature and 3.74 g (0.024 mole) of ethyl iodide was added. The reaction was monitored by thin layer chromatography (TLC) in a one to 19 mixture of methanol and ethyl acetate. Upon completion the reaction was quenched with water extracted with ether, and washed with saturated sodium bicarbonate. After drying and removal of the solvent, 5.9 g (88% yield) of a thick oil remained, Example 18 of Table 1.

EXAMPLE 177 (Procedure D)

Benzyl 2-(4-chlorophenyl)-2-[(1,2,4-triazol-1-yl)methyl]butyrate

To a 300 mL flask stirring under nitrogen was charged 4.19 g (0.015 mole) of 2-(4-chlorophenyl)-2-[(1,2,4-triazol-1-yl)methyl]-butanoic acid in 75 mL of methyl ethyl ketone. To the slurry was added 2.83 g (0.0157 mole) of potassium carbonate and the mixture was heated to reflux. After 30 minutes, 2.56 g (0.01575 mole) of benzyl bromide was added and the mixture was stirred at reflux for 2 hours then at 50° C. for 12 hours. After monitoring by GLC showed the consumption of starting material, the reaction was quenched by adding 20 mL of saturated sodium bicarbonate and 100 mL of ether. The phases were separated and the ether phase was washed with saturated sodium bicarbonate (2×50 mL) then with 50 mL of brine, dried and concentrated, giving 4.26 g (77% yield) of a thick oil, Example 177 of Table 1.

EXAMPLE 127 (Procedure D)

Methyl 4-(4-chlorophenyl)-2-phenyl-2-[(1,2,4-triazol-1-yl)methyl]-butyrate

To a 3 liter flask stirring under nitrogen was charged 276 g (2.0 mole) of potassium carbonate and 1000 mL of methyl ethyl ketone. The mixture was stirred for 10 minutes, then a cloudy solution of 356 g (1.0 moles) of 4-(4-chlorophenyl)-2-phenyl-2-[(1,2,4-triazol-1-yl)-methyl]-butanoic acid in 2000 mL of dimethyl formamide was charged and stirred at room temperature for 30 minutes. To the mixture was added 284 g (2.0 moles) of methyl iodide in 125 mL of methyl ethyl ketone over 1 hour. The reaction was stirred at room temperature for 16 hours after which TLC indicated the reaction was complete. The solvent was removed under vacuum, then the residue was treated with 2000 mL of ethyl acetate and washed with 2×1000 mL of water, dried and concentrated. The residue crystallized on concentration and was washed several times with hexane, filtered and washed with additional hexane and gave 356 g (96% yield) of pale yellow solid, Example 127 of Table 1.

EXAMPLE 137 (Procedure D)

Allyl 4-(4-chlorophenyl)-2-phenyl-2-[(1,2,4-triazol-1-yl)methyl]butyrate

To a 250 mL flask stirring under nitrogen was charged 3.55 g (0.010 mole) of a 4-(4-chlorophenyl)-2-phenyl-2-[(1,2,4-triazol-1-yl)methyl]butanoic acid in 40 mL of methyl ethyl ketone and 10 mL of dimethyl formamide. To the mixture was added 2.07 g (0.015 mole) of potassium carbonate and 1.85 g (0.011 mole) of allyl iodide. The reaction was stirred for 16 hours at 45° C. The reaction was quenched by adding 150 mL of ether and 25 mL of water. The organic phase was washed with 50 mL of saturated sodium bicarbonate and 20 mL of 10% sodium hydroxide, then 50 mL of water. After decolorizing with charcoal, the solvent was filtered and concentrated and gave 2.9 g (79.4% yield) of a solid, Example 137 of Table 1.

EXAMPLE 160 (Procedure E)

N,N-dimethyl 2-(4-chlorophenyl)-2-[(1,2,4-triazol-1-yl)methyl]-hexanamide

To a 100 mL 3 neck flask stirring under nitrogen was charged 1.5 g (0.9375 mole) 60% sodium hydride (prewashed with hexanes) in 50 mL of dimethyl formamide. To the slurry was charged 3.83 g (0.0125 mole) of 2-(4-chlorophenyl)-2-[(1,2,4-triazol-1-yl)methyl]hexanamide in 50 mL of dimethyl formamide. The mixture was sitrred at room temperature for 3 hours then quenched by adding 20 mL of water and 75 mL of ether. The ether was washed with 50 mL water and the aqueous phase was extracted with 50 ml ethyl acetate. The ether was dried and concentrated and gave 1.88 g (45.1% yield) of product as an oil, Example 160 of Table 1.

EXAMPLES 179A and 179B (Procedure E").

N-R(2-butan-1-ol)R,S-(4-(4-chlorophenyl))-2-phenyl-2-[(1,2,4-triazol-1-yl) methyl]butyramide To a stirred suspension of 4-(4-chlorophenyl)-2-phenyl-2-[(1,2,4-triazol-1-yl)methyl]butanoic acid (15 g, 42.1 mmol) in 200 mL of toluene was added 10 drops of dimethyl formamide as a catalyst. The suspension was heated to 50° C. and thionyl chloride (4.5 mL, 61.2 mmol) was added dropwise over a 2 minute period. The temperature was maintained at 50° C. for 3 hours and was then brought to 0° C. for 30 minutes. The solid material was removed by filtration and partially dried. The wet cake was quickly transferred to a round-bottom flask and used directly for the next step.

To a stirred suspension of the acid chloride in 200 mL of a 1 to 1 mixture of toluene and methylene chloride was added R-(-)-2-amino-1-butanol (18.2 mL, 194 mmol) dropwise at room temperature. The mixture was allowed to stir overnight at room temperature and then dilute hydrochloric acid was added. The organic layer was separated and washed with dilute hydrochloric acid, dilute sodium carbonate, and water. The organic layer was dried over magnesium sulfate and rotary evaporated to provide 16.6 g (90% yield from acid) of a light brown viscous oil.

The diastereomers were separated by flash chromatography over silica gel using a 20 mL to 3 drops mixture of ethyl acetate and acetic acid as the eluent. To a 20×3.2 cm column was applied 3.0 gm of the amide mixture. The first eluent band was contained in fractions #21 through #34 (15 mL cuts) and the second eluent band came after fraction #39. Repeated use of this technique on the remainder of the crude material eventually gave 6.09 g of the higher Rf band (0.33) and 3.76 g of the lower Rf (0.20) in an 84:16 ratio of diastereomers as yellow viscous oils, Examples 179A and 179B of Table 1.

EXAMPLE 94 (Procedure A')

3-benzyl-3-[(1,2,4-triazol-1-yl)methyl]-2(3H)-benzofuranone

A mixture of 2-benzyl-(2-methoxyphenyl)-1H-1,2,4-triazole-1-propanenitrile (16 g, 0.0490 mole) and hydrobromic acid (48%) (50 g, 0.296 mole) was stirred in a 300 ml round bottom flask at reflux for 96 hours. The resulting reaction mixture was cooled to room temperature and poured slowly into a solution of sodium carbonate (30 g, 0.283 mole) in 200 mL of water. The white precipitated solid was filtered by suction and washed by 100 mL water, 100 mL hexane and 100 mL ethyl ether respectively. After drying, the collected product weighed 14 g, melting point 150° C., Example 94 of Table 1.

EXAMPLE 95 (Procedure B')

2-(2-methoxyphenyl)-3-phenyl-2-[(1,2,4-triazol-1-yl)methyl]propanoic acid

To a clear solution of 3-benzyl-3-[(1,2,4-triazol-1-yl)methyl]-2(3H)-benzofuranone (11 g, 0.0360 mole) and methanol (100 mL), potassium hydroxide (45% solution) (0.5 g, 0.0750 mole) was added and the reaction mixture heated with stirring at reflux for 3 hours. The reaction mixture was then cooled to 25° C. and iodomethane (6.1 g, 0.0750 mole) added and the reaction mixture continued to stir at 50° C. for an additional 3 hours. The reaction solvent was then removed by distillation, and the residue stirred with hydrochloric acid (5 g, 0.37 mole) and 100 mL of water. The precipitated solid was filtered by suction and washed by 100 mL of hot ethyl acetate. The remaining solid was dried and gave 7.0 g, melting point 250°–252° C. (yield 57%), Example 95 of Table 1.

EXAMPLE 100 (Procedure C')

Propyl 2-(2-methoxyphenyl)-3-phenyl-2-[(1,2,4-triazol-1-yl)methyl]-propionate

A mixture of 2-(2-methoxyphenyl)-3-phenyl-2-[(1,2,4-triazol-1-yl)methyl]propanoic acid (6.0 g, 0.0178 mole) and potassium carbonate (3.6 g, 0.0213 mole) in methyl ethyl ketone (50 mL) was stirred and heated to reflux for 1 hour. Iodopropane (3.6 g, 0.0213 mole) was added and the mixture continued heating at reflux for an additional 4 hours and then allowed to cool to room temperature. The solvent was removed by distillation and 100 mL of water and 100 mL of ethyl acetate added. The organic phase was then separated, dried and concentrated on a rotary evaporator to afford 5.5 g of solid product (melting point 129°–130° C.; yield 82% ), Example 100 of Table 1.

EXAMPLE 106 (Procedure D')

Ethyl 2-(2-ethoxyphenyl)-3-phenyl-2-[(1,2,4-triazol-1-yl)methyl]propionate

To a clear solution of 3-benzyl-3-[(1,2,4-triazol-1-yl)methyl]-2(3H)-benzofuranone (3 g, 0.0098 mole) and methanol (20 mL), sodium hydroxide 50% (2.3 g, 0.0294 mole) was added and the reaction mixture heated with stirring at reflux for 3 hours. The solvent was then removed by distillation to complete dryness, and 100 mL of dimethyl formamide added, followed by 4.0 g of iodoethane (0.0245 mole). The reaction mixture continued heating at 50° C. for an additional 4 hours; 200 mL of cold water was added and extracted with 2×100 mL ethyl ether. The combined organic phase was then washed by brine, dried over magnesium sulfate, concentrated on a rotary evaporator to afford 3.2 g of oily concentrate product (yield 86%), Example 106 of Table 1.

EXAMPLE 69 (Procedures E'-1and E'-2)

t-Butyl 2-(2-methoxyphenyl)-3-phenyl-2-[(1,2,4-triazol-1-yl)methyl]hexanoate

To a clear solution of 3-butyl-3-[(1,2,4-triazol-1-yl)methyl]-2(3H)-benzofuranone (5.0 g, 0.0184 mole) and dimethyl formamide (20 mL) in a 300 mL round bottom flask, potassium t-butoxide (6.2 g, 0.0553 mole) was added and the reaction mixture stirred at room temperature for 5 minutes before adding methyl iodide (3.2 g, 0.0221 m). The reaction mixture was stirred with heating at 40° C. for 1 hour and 1.0 g of water was added. The stirring was continued for an additional 2 hours at 40° C., before adding 100 mL of water and 100 mL of ethyl ether for work up. The organic phase was isolated and dried over magnesium sulfate, evaporated by rotary evaporator to afford 4.0 g of oily concentrate (yield 61%), Example 69 of Table 1.

EXAMPLE 59 (Procedure F'-2)

2-(2-methoxyphenyl)-2-[(1,2,4-triazol-1-yl)methyl]hexanoic acid

A reaction mixture of methyl 2-(2-methoxyphenyl)-2-[(1,2,4-triazol-1yl)methyl]propionate (23 g, 0.0724 mole), 50% sodium hydroxide, (23 g, 0.2898 mole), water (25 mL) and dimethyl sulfoxide (50 mL) was stirred with heating to reflux for 5 hours. The solvent was removed by distillation and the residue stirred with 200 mL cold water and slowly acidified by hydrochloric acid (conc)to pH=7.0. The precipitated solid was filtered by suction and washed by ethyl ether thoroughly. After drying, the collected solid product weighed 12 g (melting point 198° C.; yield 57%), Example 59 of Table 1.

EXAMPLE 178 (Procedure L)

Ethyl 2-cyano-2-phenyl-2-[(1,2,4-triazol-1-yl)methyl]-propanoate

To a 300 mL 3 neck flask was charged 3.0 g (0.075 mole) of 60% sodium hydride, washed with 2×30 mL hexane, in 50 mL of dimethyl formamide. While stirring at room temperature, 5.67 g (0.030 mole, 1.0 eq.) of ethyl phenylcyanoacetate in 30 mL of dimethyl formamide was added over 15 minutes. The slurry was stirred for 15 minutes and 5.51 g of chloromethyl-1,2,4-triazole hydrochloride (0.036 mole) was added in two portions. The reaction was stirred overnight at room temperature after which GLC indicated 70% product. The reaction was quenched by adding 50 mL water and 20 mL of 10% hydrochloric acid. Ether was added (100 mL) and washed with 2×50 mL water, dried and concentrated and gave 3.6 g of crude product which was chromatographed on silica gel. The impurities were removed with a 1 to 3 mixture of ether and hexane and the product isolated with ethyl acetate and gave 1.66 g (20.5% yield), Example 178 of Table 1.

Numerous compounds of this invention were tested for fungicidal activity in vivo against wheat powdery mildew (WPM), wheat stem rust (WSR), rice blast (RB), rice sheath blight (RSB), and wheat leaf rust (WLR). In tests on cereals (except rice plants used for testing rice blast), the plants were trimmed about 24 hours prior to the application of the fungicide compound to provide a uniform plant height and to facilitate uniform application of the compound and inoculation with the fungus. The compounds were dissolved in a 2:1:1 mixture of water, acetone and methanol, sprayed onto the plants, allowed to dry (four to six hours) and then the plants were inoculated with the fungus. Each test utilized control plants which were sprayed with the water, acetone and methanol mixture and inoculated with the fungus. The remainder of the technique of each of the tests is given below and the results are reported in Table 4 as percent disease control (percentages of plants treated with the compounds of the present invention lacking disease signs or symptoms compared to the untreated control plants).

Wheat Powdery Mildew (WPM)

*Erysiphe graminis* (f. sp. tritici) was cultured on Pennol wheat seedlings in a controlled temperature room at 65° to 70° F. Mildew spores were shaken from the culture plants onto Pennol wheat seedlings which had been previously sprayed with the fungicide compound. The inoculated seedlings were kept in a controlled temperature room at 65° to 75° F. and subirrigated. The percent disease control was rated 8 to 10 days after the inoculation.

Wheat Stem Rust (WSR)

*Puccinia graminis* (f. sp. tritici Race 15B-2) was cultured on Wanzer wheat seedlings for a period of 14 days in a greenhouse. A water suspension of the spores from infested plants was obtained and the spore concentration was adjusted to about 2×10⁵ spores per ml of deionized water. Wanzer wheat plants which had been previously treated with the fungicide compounds were inoculated by applying the stem rust spore suspension, until runoff, with a DeVilbiss atomizer at 5 lbs. per square inch air pressure. After inoculation, the plants were placed in a humid environment at approximately 75° F. where they were exposed to 12 hours of continuous darkness followed by a minimum of 3 to 4 hours of light having an intensity of about 500 footcandles. The temperature in the chamber did not exceed 85° F. At the end of the light period, the plants were placed in a greenhouse where they were permitted to grow for a period of two weeks at which time the percent disease control was determined.

Rice Blast (RB)

Nato rice plants were inoculated with *Piricularia oryzae* (about 20,000 conidia per ml) by spraying the leaves and stems with an airbrush until a uniform film of inoculum was observed on the leaves. The inoculated plants were incubated in a humid environment (75° to 85° F.) for about 24 hours, then placed in a greenhouse environment (70° to 75° F.). Seven to eight days after inoculation, the percent disease control was determined.

Rice Sheath Blight (RSB)

*Pellicularia filamentosa* f. sp. sasiki was cultured on an autoclaved mixture of crushed rice seeds and potato dextrose broth (100 gms of rice seeds per 30 ml of potato dextrose broth) in a 500 ml Erlenmeyer flask. After 10 days, the culture was blended in a blender to produce a uniform inoculum. Approximately one teaspoon of inoculum was spread among Lebonnet rice seedlings on the soil surface of each pot (3 inch diameter). The inoculated seedlings were incubated for five days in a humidity cabinet (85° to 90° F.). Percent disease controls were determined immediately after removing the seedlings from the cabinet.

Wheat Leaf Rust (WLR)

*Puccinia recondita* (f. sp. tritici Races PKB and PLD) was cultured on 7 day old wheat (cultivar Fielder) over a 14 day period in the greenhouse. Spores were collected from the leaves with a cyclone vacuum or by settling on aluminum foil. The spores were cleaned by sieving through a 250 micron opening screen and stored or used fresh. Storage employed sealed bags in an Ultralow freezer. When stored, spores must be heat shocked for 2 minutes at 40° F. before use. A spore suspension is prepared from dry uredia by adding 20 mg (9.5 million spores) per mL of Soltrol oil. The suspension is dispensed into gelatin capsules (0.7 mL capacity) which attach to the oil atomizers. One capsule is used per fiat of twenty of the 2 inch square pots of 7 day old Fielder wheat. After waiting for at least 15 minutes for the oil to evaporate from the wheat leaves, the plants are placed in a dark mist chamber (18°–20° C. and 100% relative humidity) for 24 hours. The plants are then put in the greenhouse for the latent period and scored after 10 days for disease levels. For protective and curative tests, the plants are inoculated one day or two days, respectively, before spraying the plants with the fungicide compounds.

TABLE 4

Fungicidal Efficacy of Compounds of the Invention

| Ex. No. | Rate[1] | RB[2] | RSB[3] | WLR[4] | WPM[5] | WSR[6] |
|---|---|---|---|---|---|---|
| 1 | a | 50 | 0 | 0 | 99 | 50 |
| 2 | b | 0 | 100 | 100 | 100 | 90 |
| 3 | b | 90 | 80 | 100 | 99 | 100 |
| 4 | b | 90 | 100 | 100 | 99 | 100 |
| 6 | b | 0 | — | 25 | 85 | — |
| 7 | b | 0 | — | 0 | 0 | — |
| 8 | b | 0 | — | 25 | 100 | — |
| 9 | b | 50 | — | 50 | 95 | — |
| 10 | b | 75 | — | 25 | 75 | — |
| 11 | b | 0 | — | 25 | 95 | — |
| 12 | c | 0 | 0 | — | 45 | 0 |
| 13 | c | 65 | 0 | — | 100 | 92 |
| 14 | a | 0 | 0 | 0 | 85 | — |
| 15 | a | 0 | 0 | 0 | 90 | — |
| 16 | c | 40 | 0 | 0 | 85 | 80 |
| 17 | b | 80 | 0 | 85 | 100 | 100 |
| 18 | b | 0 | 0 | — | 100 | 100 |
| 19 | b | 50 | 100 | 100 | 100 | — |
| 20 | b | 0 | 0 | — | 100 | 100 |
| 21 | b | 75 | 0 | — | 90 | 100 |
| 23 | b | 0 | 0 | — | 100 | 90 |
| 24 | b | 0 | 0 | — | 100 | 90 |
| 25 | b | 0 | 0 | — | 100 | 60 |
| 26 | b | 0 | 0 | — | 100 | 90 |
| 27 | b | 0 | 0 | — | 90 | 100 |
| 28 | b | 0 | 0 | — | 100 | 80 |
| 29 | b | 0 | 0 | — | 90 | 90 |

TABLE 4 -continued
Fungicidal Efficacy of Compounds of the Invention

| Ex. No. | Rate[1] | RB[2] | RSB[3] | WLR[4] | WPM[5] | WSR[6] |
|---|---|---|---|---|---|---|
| 30 | b | 0 | 0 | — | 95 | 75 |
| 31 | b | 50 | 50 | 99 | 100 | — |
| 32 | b | 0 | 50 | 99 | 100 | — |
| 33 | b | 0 | 0 | 99 | 100 | — |
| 34 | b | 50 | 0 | — | 95 | 99 |
| 35 | b | 0 | 50 | — | 100 | 50 |
| 36 | b | 50 | 0 | — | 100 | 100 |
| 37 | b | 0 | 0 | — | 100 | 99 |
| 38 | b | 0 | 0 | — | 100 | — |
| 39 | a | 0 | 0 | 0 | 100 | — |
| 40 | a | 50 | 0 | 95 | 100 | — |
| 41 | a | 0 | 0 | 75 | 100 | — |
| 42 | a | 0 | 0 | 85 | 100 | — |
| 43 | b | 0 | 0 | 90 | 100 | — |
| 44 | a | 0 | 0 | 85 | 100 | — |
| 45 | a | — | 0 | 0 | 99 | — |
| 46 | a | 0 | 0 | 50 | 85 | — |
| 47 | a | — | 0 | 50 | 95 | — |
| 48 | a | 0 | 0 | 0 | 95 | — |
| 49 | a | 0 | 0 | 0 | 95 | — |
| 50 | a | — | 0 | 75 | 100 | — |
| 51 | a | 95 | — | 85 | 99 | — |
| 52 | a | — | 0 | 0 | 50 | — |
| 53 | a | — | 0 | 85 | 100 | — |
| 54 | a | — | 0 | 0 | 100 | — |
| 55 | a | 0 | 0 | 0 | 95 | — |
| 56 | a | — | 0 | 0 | 90 | — |
| 57 | a | 0 | 0 | 95 | 95 | — |
| 58 | a | 80 | 0 | 50 | 99 | — |
| 59 | a | 0 | 0 | 0 | 90 | — |
| 60 | b | 0 | — | 0 | 90 | — |
| 61 | b | 25 | — | 0 | 100 | — |
| 62 | b | 0 | — | 0 | 99 | — |
| 63 | b | 0 | — | 25 | 95 | — |
| 64 | a | 0 | 0 | 0 | 95 | — |
| 65 | a | 0 | 0 | 0 | 90 | — |
| 66 | a | 0 | 0 | 0 | 90 | — |
| 67 | a | 0 | 0 | 0 | 100 | — |
| 68 | a | 100 | 0 | 0 | 90 | — |
| 69 | b | 0 | — | 80 | 100 | — |
| 70 | b | 0 | — | 0 | 95 | — |
| 71 | c | 0 | 0 | — | 98 | 100 |
| 72 | b | 50 | — | 50 | 99 | — |
| 73 | b | 0 | — | 99 | 100 | — |
| 74 | b | 95 | — | 50 | 99 | — |
| 75 | b | 50 | — | 25 | 100 | — |
| 76 | b | 50 | — | 25 | 99 | — |
| 77 | b | 50 | — | 0 | 99 | — |
| 78 | b | 90 | — | 25 | 85 | — |
| 79 | b | 0 | — | 0 | 85 | — |
| 80 | a | — | 0 | 0 | 50 | — |
| 81 | a | — | 80 | 80 | 99 | — |
| 82 | a | 80 | 0 | 0 | 95 | — |
| 83 | b | 0 | — | 50 | 99 | — |
| 84 | b | 0 | — | 0 | 75 | — |
| 85 | b | 50 | — | 0 | 85 | — |
| 86 | b | 0 | — | 0 | 99 | — |
| 87 | b | 0 | — | 0 | 95 | — |
| 88 | b | 0 | — | 25 | 100 | — |
| 90 | b | 75 | — | 50 | 100 | — |
| 91 | b | 50 | — | 50 | 99 | — |
| 92 | b | 0 | — | 0 | 0 | — |
| 93 | b | 50 | — | 0 | 95 | — |
| 94 | b | 0 | — | 50 | 75 | — |
| 95 | a | 0 | — | 0 | 50 | — |
| 96 | d | — | — | 75 | 75 | — |
| 97 | b | 0 | — | 25 | 99 | — |
| 98 | b | 0 | — | 0 | 95 | — |
| 99 | b | 0 | — | 50 | 99 | — |
| 100 | a | — | 0 | 0 | 99 | — |
| 101 | a | — | 0 | 0 | 95 | — |
| 102 | a | — | 0 | 0 | 50 | — |
| 105 | b | 0 | — | 0 | 75 | — |
| 106 | b | 0 | — | 0 | 95 | — |
| 107 | b | 50 | — | 0 | 85 | — |
| 108 | b | 0 | — | 50 | 99 | — |
| 109 | b | 0 | — | 0 | 85 | — |
| 110 | b | 0 | — | 0 | 85 | — |
| 111 | b | 0 | — | 50 | 99 | — |
| 112 | b | 75 | — | 80 | 95 | — |
| 113 | b | 75 | — | 0 | 99 | — |
| 114 | b | 0 | — | 0 | 95 | — |
| 115 | b | 0 | — | 0 | 75 | — |
| 116 | b | 50 | — | 0 | 75 | — |
| 117 | b | 0 | — | 0 | 85 | — |
| 118 | b | 0 | — | 50 | 85 | — |
| 119 | b | 0 | — | 25 | 75 | — |
| 120 | b | 0 | — | 0 | 85 | — |
| 121 | b | 0 | — | 0 | 95 | — |
| 122 | b | 0 | — | 0 | 95 | — |
| 123 | a | — | — | 0 | 0 | — |
| 124 | a | — | — | 0 | 50 | — |
| 125 | a | — | — | 0 | 95 | — |
| 126 | a | 0 | 0 | 50 | 0 | — |
| 127 | a | — | 0 | 99 | 100 | — |
| 128 | b | — | — | 90 | 99 | — |
| 129 | a | 80 | 0 | 0 | 99 | — |
| 130 | a | — | 0 | 85 | 95 | — |
| 131 | a | — | 0 | 95 | 95 | — |
| 132 | a | — | 0 | 85 | 95 | — |
| 133 | a | 0 | 0 | 95 | 95 | — |
| 123 | a | 50 | 0 | 85 | 90 | — |
| 135 | a | — | 90 | 99 | 95 | — |
| 136 | a | 0 | 80 | 85 | 95 | — |
| 137 | a | 0 | 80 | 99 | 99 | — |
| 138 | a | 0 | 0 | 99 | 95 | — |
| 139 | a | 0 | 0 | 50 | 100 | — |
| 140 | a | — | 0 | 50 | 100 | — |
| 141 | a | 0 | — | 80 | 100 | — |
| 142 | a | 0 | 0 | 0 | 100 | — |
| 143 | a | 90 | 0 | 0 | 90 | — |
| 144 | a | 0 | 0 | 50 | 100 | — |
| 145 | b | 0 | — | 0 | 95 | — |
| 146 | a | — | 90 | 0 | 75 | — |
| 147 | b | 0 | — | 99 | 99 | — |
| 148 | a | — | 80 | 50 | 95* | — |
| 149 | a | — | 0 | 50 | 90 | — |
| 150 | a | — | 0 | 0 | 0 | — |
| 151 | a | — | 0 | 0 | 80 | — |
| 152 | a | — | 0 | 0 | 80 | — |
| 153 | a | 0 | 0 | 0 | 100 | — |
| 154 | a | — | — | — | — | — |
| 155 | c | 80 | 40 | — | 98 | 98 |
| 156 | a | — | 0 | 0 | 75 | — |
| 157 | c | 0 | 35 | — | 72 | 70 |
| 158 | a | 0 | 0 | 0 | 95 | — |
| 159 | b | 0 | 0 | — | 100 | 70 |
| 160 | a | 50 | 0 | 0 | 95 | — |
| 161 | a | 0 | 0 | 95 | 100 | — |
| 162 | b | 0 | 100 | — | — | 70 |
| 163 | a | — | 0 | 50 | 0 | — |
| 164 | a | 0 | 50 | 0 | 0 | — |
| 165 | a | 0 | 0 | 0 | 75 | — |
| 166 | a | 0 | 0 | — | 80 | — |
| 167 | a | 0 | 0 | 0 | 85 | — |
| 168 | b | 0 | — | 0 | 50 | — |
| 169 | b | 0 | — | 0 | 95 | — |
| 170 | a | 0 | 0 | 75 | 75 | — |
| 171 | b | 0 | — | 99 | 99 | — |
| 172 | b | 0 | — | 90 | 95 | — |
| 173 | b | 0 | — | 25 | 95 | — |
| 174 | b | 0 | — | 90 | 95 | — |
| 175 | b | 0 | — | 80 | 90 | — |
| 176 | b | 0 | — | 90 | 90 | — |
| 177 | b | 0 | — | 99 | 99 | — |
| 178 | a | 0 | 0 | 0 | 100 | — |

[1]Test rate: a = 100 PPM; b = 200 PPM; c = 300 PPM; d = 600 PPM
[2]rice blast (*Piricularia oryzae*)
[3]rice sheath blight (*Pellicularia filamentosa* f. sp. sasiki)
[4]wheat leaf rust (*Puccinia recondita* (f. sp. tridci Races PKB and PLD))
[5]wheat powdery mildew (*Erysiphi graminis* f.sp. tritici)
[6]wheat stem rust (*Puccinia graminis* f. sp. tritici)
[7]not tested The compounds of this invention were also tested for pre- and post-emergent herbicidal activity against the following species:

| CODE | COMMON NAME | SCIENTIFIC NAME |
|------|-------------|-----------------|
|      |             | MONOCOTS |
| BYG  | Barnyardgrass | *Echinochloa crus-galli* |
| FOX  | Foxtail | *Setaria viridis* |
| JON  | Johnsongrass | *Sorghum halepense* |
| NUT  | Nutsedge | *Cyperus esculentus* |
| WO   | Wild Oat | *Avena fatua* |
|      |             | DICOTS |
| CKL  | Cocklebur | *Xanthium strumarium* |
| MG   | Morning glory | *Ipomoea lacunosa* |
| PIG  | Pigweed | *Amaranthus retroflexus* |
| VEL  | Velvetleaf | *Abutilon theophrastic* |

The following test procedure was employed. Seeds of selected plants were planted in flats or pots. For pre-emergence tests, immediately after planting, the test compound was sprayed directly onto the soil surface. The flats or pots were then placed in a greenhouse and watered by subirrigation and overhead. Subsequently, only overhead watering was used. For post-emergence tests, the seeds were allowed to germinate and grow in a green house for 14 to 21 days. Before application, each series of test plants were selected for uniformity, size and stage of development. The test plants were then treated with the test compound. The plants for post-emergence tests were returned to the greenhouse and then watered by subirrigation only.

The compound to be evaluated was dissolved in an appropriate solvent, usually acetone, and sprayed over the flats or pots using a carrier volume equivalent to 25 or 50 gallons per acre at the rate of application in pounds per acre (lb/A) specified in Table 5 (usually 4 lb/A). The results are reported in Table 5 for each species. About two or three weeks after application of the test compound, the state of growth of the plants were observed. Each species was evaluated on a scale of 0–100 in which 0 equals no activity and 100 equals total control.

TABLE 5

Herbicidal Efficacy of Selected Compounds of the Invention
Pre- and post-emergent percent control of various weeds at indicated test rates is shown

| Ex # | Rate | P/P | CKL | MG | PIG | VEL | BYG | FOX | JON | NUT | WO |
|------|------|-----|-----|-----|-----|-----|-----|-----|-----|-----|-----|
| 2 | 4 | Pre  | 0  | 21  | 100 | 86 | 71 | 86 | 96 | 0   | 11 |
| 2 | 4 | Post | 0  | 30  | 66  | 10 | 10 | 10 | 0  | 0   | 0  |
| 3 | 4 | Pre  | 31 | 100 | 71  | 85 | 95 | 91 | 41 | 0   | 0  |
| 3 | 4 | Post | 0  | 0   | 0   |    | 16 | 0  | 0  | 0   | 0  |
| 4 | 4 | Pre  | 0  | 11  | 100 | 21 | 81 | 86 | 86 |     | 21 |
| 4 | 4 | Post | 0  | 0   | 0   | 0  | 15 | 5  | 0  | 0   | 0  |
| 9 | 4 | Pre  | 0  | 81  | 100 | 21 | 98 | 91 | 81 | 0   | 71 |
| 9 | 4 | Post | 18 | 25  | 100 | 20 | 17 | 51 | 11 | 51  | 41 |
| 10 | 4 | Pre  | 0  | 31  | 100 | 11 | 95 | 98 | 81 | 100 | 51 |
| 10 | 4 | Post | 41 | 55  | 100 | 60 | 40 | 15 | 20 | 0   | 0  |
| 11 | 4 | Pre  | 0  | 0   |     | 0  | 61 | 91 | 71 | 0   | 11 |
| 11 | 4 | Post | 41 | 51  | 100 | 20 | 51 | 51 | 51 | 11  | 0  |
| 13 | 4 | Pre  | 21 | 21  | 11  | 21 | 11 | 21 | 90 | 0   | 11 |
| 13 | 4 | Post | 10 | 46  | 16  | 20 | 0  | 0  | 0  | 0   | 20 |
| 14 | 4 | Pre  | 0  | 0   | 100 | 0  | 21 | 71 | 41 | 0   | 0  |
| 14 | 4 | Post | 5  | 25  | 0   | 45 | 10 | 0  | 20 | 0   | 0  |
| 15 | 4 | Pre  | 0  | 0   | 100 | 0  | 61 | 22 | 31 | 11  | 0  |
| 15 | 4 | Post | 3  | 35  | 0   | 10 | 0  | 0  | 5  | 0   | 0  |
| 17 | 2 | Pre  | 0  | 100 | 100 | 0  | 95 | 96 | 86 | 61  | 0  |
| 17 | 2 | Post | 0  | 36  | 26  | 31 | 0  | 0  | 0  | 0   | 0  |
| 18 | 2 | Pre  | 0  | 0   | 100 | 0  | 90 | 10 | 66 | 0   | 95 |
| 18 | 2 | Post | 0  | 26  | 26  | 0  | 0  | 0  | 0  | 0   | 0  |
| 20 | 4 | Pre  | 0  | 27  | 100 | 0  | 41 | 5  | 0  | 0   |    |
| 20 | 4 | Post | 0  | 45  | 26  | 41 | 0  | 0  | 0  | 0   | 0  |
| 21 | 4 | Pre  | 0  | 0   | 71  | 0  | 0  | 15 | 0  | 0   | 0  |
| 21 | 4 | Post | 0  | 51  | 46  | 21 | 0  | 0  | 0  | 0   | 0  |
| 22 | 4 | Pre  | 0  | 0   | 0   | 0  | 0  | 0  | 0  | 0   | 0  |
| 22 | 4 | Post | 5  | 0   | 0   | 0  | 0  | 0  | 0  | 0   | 0  |
| 24 | 4 | Pre  | 0  | 0   | 0   | 0  | 0  | 0  | 0  | 0   | 0  |
| 24 | 4 | Post | 10 | 15  |     | 0  | 0  | 0  | 0  | 0   | 0  |
| 25 | 4 | Pre  | 0  | 0   |     | 0  | 0  | 10 | 0  | 0   | 0  |
| 25 | 4 | Post | 5  | 0   |     | 0  | 0  | 0  | 0  | 0   | 0  |
| 26 | 4 | Pre  | 31 | 0   |     | 20 | 70 | 10 | 0  | 0   | 0  |
| 26 | 4 | Post | 10 | 0   | 0   | 0  | 0  | 0  | 0  | 0   | 0  |
| 27 | 4 | Pre  | 0  | 0   | 0   | 0  | 0  | 0  | 0  | 0   | 0  |
| 27 | 4 | Post | 10 | 0   | 45  | 0  | 0  | 0  | 0  | 0   | 0  |
| 28 | 4 | Pre  | 0  | 0   | 0   | 0  | 0  | 0  | 0  | 0   | 0  |
| 28 | 4 | Post | 0  | 66  | 0   | 0  | 0  | 0  | 0  |     | 0  |
| 29 | 4 | Pre  | 0  | 0   | 0   | 0  | 0  | 0  | 0  | 0   |    |
| 29 | 4 | Post | 0  | 0   | 56  | 0  | 0  | 0  | 0  | 0   | 0  |
| 31 | 4 | Pre  | 0  | 10  |     | 0  | 30 | 90 | 40 | 0   | 0  |
| 31 | 4 | Post | 15 | 76  | 0   | 0  | 5  | 10 | 0  | 0   | 0  |
| 33 | 4 | Pre  | 0  | 0   | 0   | 0  | 0  | 0  | 0  | 0   | 0  |
| 33 | 4 | Post | 10 | 0   | 0   | 0  | 0  | 0  | 0  | 0   | 0  |
| 34 | 4 | Pre  |    | 0   | 0   | 13 | 65 | 0  | 0  | 0   | 0  |
| 34 | 4 | Post | 5  | 10  | 15  | 10 | 0  | 0  | 0  | 0   | 0  |
| 35 | 4 | Pre  | 0  | 0   | 0   | 0  | 0  | 0  | 0  | 0   | 0  |
| 35 | 4 | Post | 15 | 0   | 5   | 0  | 0  | 0  | 0  | 0   | 0  |
| 36 | 4 | Pre  | 0  | 0   |     | 0  | 0  | 0  | 0  | 0   | 0  |
| 36 | 4 | Post | 5  | 0   | 5   | 10 | 0  | 0  | 0  | 0   | 0  |
| 37 | 4 | Pre  | 0  | 0   | 0   | 0  | 0  | 0  | 0  | 0   | 0  |
| 37 | 4 | Post | 15 | 0   | 26  | 0  | 0  | 0  | 0  | 0   | 0  |
| 39 | 4 | Pre  | 0  | 0   | 0   | 0  | 0  | 0  | 0  | 0   |    |

TABLE 5-continued

Herbicidal Efficacy of Selected Compounds of the Invention
Pre- and post-emergent percent control of various weeds at indicated test rates is shown

| Ex # | Rate | P/P | CKL | MG | PIG | VEL | BYG | FOX | JON | NUT | WO |
|------|------|------|-----|-----|-----|-----|-----|-----|-----|-----|-----|
| 39 | 4 | Post | 0 | 5 | 0 | | 0 | 0 | 0 | 0 | 0 |
| 40 | 4 | Pre | 0 | 70 | 100 | 80 | 100 | 100 | 95 | 0 | 71 |
| 40 | 4 | Post | 16 | 75 | 25 | 70 | 10 | 10 | 0 | 0 | 0 |
| 41 | 4 | Pre | 0 | 75 | 100 | 95 | 100 | 100 | 98 | | 61 |
| 41 | 4 | Post | 36 | 70 | 15 | 85 | 80 | 5 | 0 | 0 | 0 |
| 42 | 4 | Pre | 100 | 100 | 100 | 100 | 100 | 100 | 80 | 0 | 25 |
| 42 | 4 | Post | 66 | 66 | 56 | 76 | 65 | 61 | 0 | 0 | 0 |
| 43 | 4 | Pre | 0 | 10 | 100 | 0 | 90 | 91 | 31 | 0 | 0 |
| 43 | 4 | Post | 51 | 20 | 11 | 11 | 5 | 0 | 0 | 0 | 0 |
| 43 | 1 | Pre | 0 | 0 | 0 | 0 | 84 | 81 | 0 | 0 | 0 |
| 43 | 1 | Post | 0 | 10 | 0 | 0 | 10 | 5 | 0 | 0 | 0 |
| 44 | 4 | Pre | 11 | 21 | 0 | 21 | 98 | 80 | 21 | 0 | 11 |
| 44 | 4 | Post | 20 | 35 | | 15 | 15 | 0 | 0 | 0 | 0 |
| 46 | 2 | Pre | 0 | 0 | 61 | 0 | 0 | 0 | 0 | 0 | 0 |
| 46 | 2 | Post | 16 | 40 | 16 | 0 | 0 | 0 | 0 | 0 | 0 |
| 47 | 4 | Pre | 0 | 0 | 0 | 26 | 70 | 95 | 41 | 0 | 0 |
| 47 | 4 | Post | 46 | 0 | 16 | 16 | 10 | 0 | 0 | 0 | 0 |
| 48 | 4 | Pre | 0 | 0 | 100 | 11 | 90 | 35 | 21 | 0 | 0 |
| 48 | 4 | Post | 0 | 0 | 0 | 0 | 0 | 0 | 0 | 0 | 0 |
| 49 | 4 | Pre | 0 | 0 | 100 | 0 | 90 | 45 | 11 | 0 | 0 |
| 49 | 4 | Post | 0 | 0 | 0 | 0 | 10 | 0 | 0 | 0 | 0 |
| 50 | 4 | Pre | 0 | 21 | | 36 | 85 | 11 | 0 | 0 | 0 |
| 50 | 4 | Post | 0 | 25 | | 40 | 45 | 0 | 0 | 0 | 0 |
| 51 | 4 | Pre | 0 | 0 | 100 | 21 | 98 | 80 | 71 | 21 | 31 |
| 51 | 4 | Post | 15 | 0 | 25 | 0 | 25 | 10 | 0 | 0 | 0 |
| 53 | 4 | Pre | 0 | | 0 | 0 | 95 | 90 | 0 | 0 | 11 |
| 53 | 4 | Post | 15 | 10 | | 15 | 0 | 0 | 0 | 0 | 0 |
| 56 | 4 | Pre | 0 | 85 | 0 | 0 | 75 | 15 | 0 | 0 | 0 |
| 56 | 4 | Post | 0 | 10 | 0 | 0 | 0 | 0 | 0 | 0 | 0 |
| 57 | 4 | Pre | 0 | 0 | 100 | 26 | 81 | 99 | 41 | 0 | 0 |
| 57 | 4 | Post | 36 | 56 | 26 | 16 | 61 | 0 | 0 | 0 | 0 |
| 58 | 4 | Pre | 0 | 0 | 100 | 100 | 90 | 90 | 0 | 0 | 0 |
| 58 | 4 | Post | 15 | 15 | 10 | 15 | 0 | 0 | 0 | 0 | 0 |
| 59 | 4 | Pre | 0 | 0 | 0 | 0 | 0 | 0 | 0 | 0 | 0 |
| 59 | 4 | Post | 0 | 0 | 0 | 0 | 0 | 15 | 0 | 0 | 0 |
| 61 | 4 | Pre | 41 | 51 | 21 | 31 | 100 | 100 | 81 | | 71 |
| 61 | 4 | Post | 80 | 85 | 90 | 76 | 71 | 25 | 35 | 61 | 0 |
| 62 | 4 | Pre | 0 | 76 | 100 | 61 | 91 | 100 | 81 | 100 | 61 |
| 62 | 4 | Post | 86 | 86 | | 56 | 75 | 25 | 11 | 41 | 0 |
| 63 | 4 | Pre | 0 | 36 | 41 | 16 | 98 | 100 | 61 | 0 | 41 |
| 63 | 4 | Post | 31 | 76 | 46 | 66 | 35 | 26 | 0 | 0 | 0 |
| 65 | 4 | Pre | 0 | 56 | 21 | 11 | 100 | 91 | 91 | 91 | 61 |
| 65 | 4 | Post | 0 | 5 | 0 | 21 | 55 | 21 | 11 | 0 | 0 |
| 66 | 4 | Pre | 0 | 56 | 21 | 11 | 99 | 91 | 81 | 100 | 41 |
| 66 | 4 | Post | 21 | 15 | 0 | 21 | 45 | 21 | 21 | 0 | 0 |
| 67 | 4 | Pre | 0 | 56 | 21 | 11 | 99 | 81 | 81 | 0 | 51 |
| 67 | 4 | Post | 0 | 10 | 0 | 31 | 40 | 21 | 21 | 0 | 0 |
| 69 | 4 | Pre | 0 | 61 | 41 | 31 | 81 | 100 | 81 | 71 | 71 |
| 69 | 4 | Post | 80 | 65 | 100 | 60 | 37 | 31 | 25 | 0 | 21 |
| 70 | 4 | Pre | 0 | 0 | 100 | 0 | 71 | 51 | 21 | 0 | 0 |
| 70 | 4 | Post | 0 | 0 | 0 | 0 | 0 | 0 | 0 | 0 | 0 |
| 72 | 4 | Pre | 0 | 61 | 21 | 21 | 100 | 100 | 91 | | 71 |
| 72 | 4 | Post | 60 | 85 | 26 | 71 | 71 | 51 | 71 | 0 | 0 |
| 74 | 4 | Pre | 0 | 10 | 100 | 10 | 98 | 99 | 40 | 21 | 0 |
| 74 | 4 | Post | 51 | 90 | 100 | 80 | 0 | 71 | 11 | | 0 |
| 75 | 4 | Pre | 0 | 0 | 0 | 0 | 95 | 100 | 71 | 21 | 61 |
| 75 | 4 | Post | 61 | 35 | 100 | 25 | 27 | 0 | 0 | 0 | 0 |
| 76 | 4 | Pre | 0 | 76 | 100 | 25 | 95 | 100 | 71 | | 31 |
| 76 | 4 | Post | 61 | 70 | | 76 | 65 | 0 | 0 | 0 | 0 |
| 77 | 4 | Pre | 0 | 0 | 0 | 0 | 95 | 95 | 0 | 0 | 0 |
| 77 | 4 | Post | 40 | 90 | 95 | 85 | 31 | 10 | 31 | | 0 |
| 78 | 4 | Pre | 0 | 0 | 25 | 0 | 95 | 91 | 0 | 51 | 0 |
| 78 | 4 | Post | 31 | 95 | 35 | 30 | 0 | 10 | 0 | | 0 |
| 79 | 4 | Pre | 0 | 75 | 0 | 50 | 100 | 91 | 91 | 81 | 71 |
| 79 | 4 | Post | 51 | 90 | 90 | 90 | 31 | 95 | 31 | | 25 |
| 81 | 4 | Pre | 0 | 81 | 0 | 0 | 71 | | 31 | 0 | 0 |
| 81 | 4 | Post | 15 | 71 | 31 | 71 | 0 | 0 | 0 | 0 | 0 |
| 82 | 4 | Pre | 0 | 0 | 0 | | 41 | 0 | 21 | 0 | 0 |
| 82 | 4 | Post | 20 | 51 | 0 | 0 | 0 | 0 | 0 | 0 | 0 |
| 86 | 4 | Pre | 21 | 21 | 100 | 31 | 98 | 100 | 71 | 61 | 61 |
| 86 | 4 | Post | 0 | 56 | | 0 | 15 | 5 | 0 | 0 | 0 |
| 87 | 4 | Pre | 0 | 0 | 0 | 0 | 0 | 0 | 0 | 0 | 0 |
| 87 | 4 | Post | 0 | 10 | | 0 | 0 | 0 | 0 | 0 | 0 |
| 88 | 4 | Pre | 0 | 66 | 100 | 0 | 81 | 100 | 71 | 61 | 21 |
| 88 | 4 | Post | 0 | 26 | | 11 | 0 | 0 | 0 | 0 | 0 |
| 90 | 4 | Pre | 0 | 0 | 90 | 0 | 71 | 100 | 41 | 0 | 31 |
| 90 | 4 | Post | 10 | 0 | 0 | 0 | 0 | 0 | 0 | 0 | 0 |
| 91 | 2 | Pre | 0 | 0 | 75 | 0 | 81 | 95 | 21 | 0 | 11 |

TABLE 5-continued

Herbicidal Efficacy of Selected Compounds of the Invention
Pre- and post-emergent percent control of various weeds at indicated test rates is shown

| Ex # | Rate | P/P | CKL | MG | PIG | VEL | BYG | FOX | JON | NUT | WO |
|---|---|---|---|---|---|---|---|---|---|---|---|
| 91 | 2 | Post | 10 | 65 | 0 | 0 | 5 | 0 | 5 | 0 | 0 |
| 93 | 4 | Pre | 0 | 66 | 100 | 31 | 100 | 100 | 81 | | 71 |
| 93 | 4 | Post | 46 | 61 | 31 | 71 | 51 | 41 | 71 | 0 | 0 |
| 94 | 4 | Pre | 0 | 0 | 100 | 0 | 45 | 90 | 61 | 0 | 0 |
| 94 | 4 | Post | 0 | 0 | 0 | 0 | 0 | 0 | 0 | 0 | 0 |
| 95 | 4 | Pre | 0 | 0 | 0 | 0 | 0 | 20 | 0 | | 0 |
| 95 | 4 | Post | 0 | 15 | 0 | 0 | 0 | 0 | 0 | 0 | 0 |
| 97 | 4 | Pre | 21 | 75 | 100 | 42 | 100 | 100 | 91 | | 71 |
| 97 | 4 | Post | 25 | 51 | 36 | 61 | 51 | 51 | 71 | 21 | 0 |
| 98 | 4 | Pre | 31 | 41 | 100 | 31 | 100 | 100 | 91 | 21 | 71 |
| 98 | 4 | Post | 75 | 51 | 0 | 61 | 51 | 51 | 11 | 21 | 0 |
| 99 | 4 | Pre | 0 | 76 | 71 | 16 | 100 | 90 | 80 | 0 | 0 |
| 99 | 4 | Post | 25 | 75 | 16 | 16 | 0 | 5 | 0 | 0 | 0 |
| 100 | 4 | Pre | 0 | 46 | 0 | 16 | 100 | 95 | 80 | 0 | 41 |
| 100 | 4 | Post | 41 | 21 | 21 | 10 | 15 | 15 | 31 | 0 | 0 |
| 101 | 4 | Pre | 0 | 85 | 100 | 0 | 100 | 98 | 85 | 81 | 61 |
| 101 | 4 | Post | 51 | 31 | 11 | 15 | 10 | 31 | 31 | 0 | 0 |
| 106 | 4 | Pre | 0 | 0 | | 0 | 98 | 100 | 81 | 0 | 71 |
| 106 | 4 | Post | 51 | 61 | 11 | 51 | 61 | 41 | 61 | 31 | 0 |
| 107 | 4 | Pre | 0 | 61 | 100 | 21 | 95 | 98 | 71 | 0 | 61 |
| 107 | 4 | Post | 61 | 35 | 100 | 30 | 17 | 21 | 11 | 0 | 0 |
| 108 | 4 | Pre | 0 | 71 | 61 | 11 | 98 | 81 | 71 | 0 | 61 |
| 108 | 4 | Post | 61 | 45 | 100 | 15 | 21 | 0 | 0 | 0 | 0 |
| 110 | 4 | Pre | 0 | 61 | 100 | 0 | 71 | 98 | 71 | 0 | 51 |
| 110 | 4 | Post | 51 | 25 | 100 | 20 | 27 | 0 | 0 | 0 | 0 |
| 111 | 4 | Pre | 0 | 31 | 100 | 0 | 98 | 95 | 71 | 0 | 31 |
| 111 | 4 | Post | 61 | 15 | 20 | 30 | 27 | 0 | 0 | 0 | 0 |
| 112 | 4 | Pre | 0 | 61 | 100 | 21 | 98 | 100 | 51 | 0 | 31 |
| 112 | 4 | Post | 51 | 45 | 100 | 45 | 67 | 0 | 21 | 0 | 0 |
| 114 | 4 | Pre | 0 | 61 | 100 | 0 | 98 | 100 | 51 | 0 | 61 |
| 114 | 4 | Post | 51 | 35 | 100 | 25 | 27 | 0 | 0 | 0 | 0 |
| 115 | 4 | Pre | 0 | 0 | 0 | 0 | 90 | 85 | 61 | 0 | 21 |
| 115 | 4 | Post | 51 | 35 | 100 | 25 | 17 | 0 | 0 | 0 | 0 |
| 116 | 4 | Pre | 21 | 26 | | 11 | 98 | 90 | 81 | 0 | 21 |
| 116 | 4 | Post | 51 | 15 | 81 | 15 | 20 | 0 | 51 | 0 | 0 |
| 117 | 4 | Pre | 21 | 61 | | 11 | 98 | 99 | 91 | | 51 |
| 117 | 4 | Post | 51 | 71 | 91 | 51 | 45 | 21 | 71 | 25 | 0 |
| 118 | 4 | Pre | 11 | 21 | 21 | 0 | 95 | 98 | 71 | 0 | 0 |
| 118 | 4 | Post | 0 | 20 | 36 | 16 | 0 | 0 | 0 | 0 | 0 |
| 119 | 4 | Pre | 0 | 36 | 100 | 0 | 85 | 80 | 81 | 0 | 0 |
| 119 | 4 | Post | 85 | 66 | 16 | 16 | 60 | 20 | 21 | 0 | 0 |
| 120 | 4 | Pre | 0 | 46 | 0 | 0 | 90 | 90 | 71 | 0 | 0 |
| 120 | 4 | Post | 41 | 61 | 0 | 0 | 0 | 0 | 0 | 0 | 0 |
| 121 | 4 | Pre | 0 | 0 | 0 | 0 | 90 | 95 | 71 | 0 | 0 |
| 122 | 4 | Pre | 0 | 76 | 100 | 0 | 100 | 100 | 100 | | 61 |
| 122 | 4 | Post | 86 | 0 | 0 | 61 | 45 | 0 | 61 | 0 | 0 |
| 124 | 4 | Pre | 0 | 0 | 11 | 0 | 71 | 81 | 0 | 0 | 0 |
| 124 | 4 | Post | 0 | 0 | 0 | 0 | 0 | 0 | 0 | 0 | 0 |
| 125 | 4 | Pre | 41 | 0 | 21 | 0 | 31 | 91 | 0 | 0 | 11 |
| 125 | 4 | Post | 15 | 0 | 0 | 0 | 0 | 0 | 0 | 0 | 0 |
| 131 | 4 | Pre | 0 | 0 | 0 | 0 | 0 | 0 | 0 | 0 | 0 |
| 131 | 4 | Post | 5 | 26 | 0 | 0 | 0 | 0 | 41 | 0 | 0 |
| 135 | 4 | Pre | | 0 | 0 | 0 | 0 | 0 | 0 | | 0 |
| 135 | 4 | Post | 5 | 20 | 0 | 0 | 0 | 0 | 31 | 0 | 0 |
| 136 | 4 | Pre | 0 | 0 | 0 | 0 | 0 | 0 | 0 | 0 | 0 |
| 136 | 4 | Post | 0 | 25 | 0 | 0 | 0 | 0 | 0 | 0 | 0 |
| 141 | 4 | Pre | 0 | 0 | 0 | 0 | 100 | 0 | 0 | 0 | 0 |
| 141 | 4 | Post | 0 | 0 | 0 | 0 | 0 | 0 | 0 | 0 | 0 |
| 145 | 4 | Pre | 0 | 0 | 0 | 0 | 0 | 0 | 0 | 0 | 0 |
| 145 | 4 | Post | 0 | 0 | 100 | 0 | 0 | 0 | 0 | 0 | 0 |
| 147 | 4 | Pre | 0 | 0 | 0 | 25 | 90 | 91 | 0 | 0 | 0 |
| 147 | 4 | Post | 61 | 95 | 50 | 40 | 31 | 0 | 11 | | 0 |
| 148 | 4 | Pre | 0 | 25 | 0 | 0 | 61 | 91 | 51 | 0 | 0 |
| 148 | 4 | Post | 25 | 5 | 20 | 0 | 0 | 0 | 0 | 0 | 0 |
| 149 | 4 | Pre | 0 | | 100 | 0 | 71 | 91 | 61 | 0 | 0 |
| 149 | 4 | Post | 35 | 5 | 15 | 5 | 0 | 0 | 0 | 0 | 0 |
| 157 | 4 | Pre | 0 | 0 | | 0 | 0 | 0 | 0 | 0 | 0 |
| 157 | 4 | Post | 0 | 0 | 6 | 0 | 0 | 0 | 0 | 0 | 0 |
| 158 | 4 | Pre | | 0 | 45 | 0 | 95 | 90 | 95 | 0 | 0 |
| 158 | 4 | Post | | 40 | 16 | 0 | 0 | 0 | 15 | 0 | 0 |
| 160 | 4 | Pre | 0 | 0 | 0 | 0 | 31 | 41 | 41 | 0 | 0 |
| 160 | 4 | Post | 0 | 0 | 0 | 0 | 0 | 0 | 0 | 0 | 0 |
| 161 | 4 | Pre | 0 | 0 | 0 | 0 | 0 | 0 | 51 | 31 | 0 |
| 161 | 4 | Post | 0 | 15 | 0 | 0 | 0 | 0 | 0 | 0 | 0 |
| 163 | 4 | Pre | 0 | 0 | 0 | 11 | 70 | 80 | 0 | 0 | 11 |
| 163 | 4 | Post | 0 | 5 | | 0 | 0 | 5 | 0 | 0 | 0 |
| 169 | 4 | Pre | 0 | 0 | 0 | 0 | 98 | 60 | 21 | 71 | 0 |

TABLE 5-continued

Herbicidal Efficacy of Selected Compounds of the Invention
Pre- and post-emergent percent control of various weeds at indicated test rates is shown

| Ex # | Rate | P/P | CKL | MG | PIG | VEL | BYG | FOX | JON | NUT | WO |
|------|------|-----|-----|-----|-----|-----|-----|-----|-----|-----|-----|
| 169 | 4 | Post | 0 | 75 | 25 | 25 | 0 | 5 | 0 | 0 | 0 |

We claim

1. A compound of the formula wherein

T is hydrogen or is one or two substituents independently selected from the group consisting of halo, trihalomethyl, $(C_1-C_4)$alkyl, phenyl, phenyl monosubstituted with halo or $(C_1-C_4)$alkyl, phenoxy and phenoxy monosubstituted with halo or $(C_1-C_4)$alkyl;

Q is 1H-(1,2,4-triazol-1-yl), 4H-(1,2,4-triazol-4-yl), or 1H-(1,2,4-triazol-1-yl) or 4H-1,2,4-triazol-4-yl) substituted with up to two substituents selected from halo, $(C_1-C_4)$alkyl, nitro, cyano, mercapto and $(C_1-C_5)$alkylmercapto;

Z is $(C_1-C_{12})$alkyl, halo$(C_1-C_{12})$alkyl, $(C_2-C_8)$alkenyl, halo$(C_2-C_8)$alkenyl, $(C_2-C_8)$alkynyl, $(C_3-C_8)$cycloalkyl, $(C_5-C_8)$cycloalkenyl, $(C_3-C_7)$cycloalkyl$(C_1-C_5)$alkyl, $(C_6-C_{10})$aryl, $(C_6-C_{10})$ar($C_1-C_4$)alkyl, $(C_6-C_{10})$aryl or $(C_6-C_{10})$ar$(C_1-C_4)$alkyl substituted on the aryl ring with with up to three substituents independently selected from the group consisting of hydroxy, halo, nitro, trihalomethyl, cyano, $(C_1-C_4)$alkyl, $(C_1-C_4)$alkoxy, $(C_1\propto C_4)$alkylthio, $(C_1-C_4)$alkylsulfinyl, $(C_1-C_4)$alkylsulfonyl, $(C_1-C_4)$alkoxy$(C_1-C_4)$alkoxy, $(C_1-C_4)$alkylcarbonyl, $(C_2-C_8)$alkenyl, $(C_2-C_4)$alkenyloxy, $(C_2-C_8)$alkynyl and $(C_2-C_8)$alkynyloxy, pyridyl$(C_1-C_2)$alkyl or thienyl$(C_1-C_2)$alkyl; or the agronomically acceptable enantiomorphs, acid addition salts and metal salt complexes thereof.

2. The compound of claim 1 wherein

T is hydrogen or one or two substituents independently selected from the group consisting of fluoro, chloro, bromo, trifluoromethyl, methyl, ethyl, phenyl, phenyl monosubstituted with fluoro, chloro, bromo, methyl or ethyl, phenoxy and phenoxy monosubstituted with fluoro, chloro, bromo, methyl or ethyl;

Q is 1H-(1,2,4-triazol-1-yl); and

Z is $(C_1-C_8)$alkyl, $(C_5-C_7)$cycloalkyl, 3-pyridylmethyl, 2-(3-pyridyl)ethyl, 2-thienylmethyl, 2-(2-thienyl)ethyl, phenyl, benzyl or phenethyl, or phenyl, benzyl or phenethyl the aromatic portion of which is substituted with 1 or 2 halo or trihalomethyl substituents.

3. The compound of claim 2 wherein

T is hydrogen, one substituent in the 3 or 4 position of the phenyl ring selected from the group consisting of fluoro, chloro, bromo, trifluoromethyl, methyl, ethyl, phenyl, phenyl monosubstituted with fluoro, chloro, bromo, methyl or ethyl, phenoxy and phenoxy monosubstituted with fluoro, chloro, bromo, methyl or ethyl, or two substituents in the 3 and 4 positions of the phenyl ring selected from the group consisting of fluoro, chloro, bromo, trifluoromethyl, methyl and ethyl; and Z is $(C_1-C_6)$alkyl, $(C_5-C_6)$cycloalkyl, phenyl, benzyl, phenethyl, or monochloro substituted phenyl, benzyl or phenethyl.

4. The compound of claim 3 wherein T is hydrogen, 3-chloro, 4-chloro, 3,4-dichloro, 3-fluoro or 4-fluoro and Z is ethyl, n-butyl, cyclopentyl, benzyl, 2-chlorobenzyl, or 4-chlorophenethyl.

5. The compound of claim 4 in which T is hydrogen and Z is n-butyl or 4-chlorophenethyl.

6. A fungicidal composition which comprises an agronomically acceptable carrier and a fungicidally effective amount of a compound of claim 1.

7. A method for controlling fungi which comprises applying to the locus where control is desired a fungicidally effective amount of a compound of claim 1.

8. A herbicidal composition which comprises an agronomically acceptable carrier and a herbicidally effective amount of a compound of claim 1.

9. A method for controlling undesirable vegetation which comprises applying to the locus where control is desired a herbicidally effective amount of a compound of claim 1.

* * * * *